(12) United States Patent
Dunham et al.

(10) Patent No.: US 12,296,392 B2
(45) Date of Patent: May 13, 2025

(54) SINGLE- AND MIXED-METAL NANOPARTICLES, NANOPARTICLE CONJUGATES, DEVICES FOR MAKING NANOPARTICLES, AND RELATED METHODS OF USE

(71) Applicant: MONTROSE BIOSYSTEMS LLC, Vista, CA (US)

(72) Inventors: Joseph P Dunham, Pasadena, CA (US); Marcus Yaffee, Pasadena, CA (US)

(73) Assignee: MONTROSE BIOSYSTEMS LLC, Vista, CA (US)

( * ) Notice: Subject to any disclaimer, the term of this patent is extended or adjusted under 35 U.S.C. 154(b) by 0 days.

(21) Appl. No.: 18/322,417

(22) Filed: May 23, 2023

(65) Prior Publication Data

US 2023/0390427 A1 Dec. 7, 2023

Related U.S. Application Data

(63) Continuation of application No. 16/758,770, filed as application No. PCT/US2018/057134 on Oct. 23, 2018, now abandoned.

(60) Provisional application No. 62/576,009, filed on Oct. 23, 2017.

(51) Int. Cl.

| | | |
|---|---|---|
| *A61K 49/00* | (2006.01) |
| *A61K 51/12* | (2006.01) |
| *B22F 1/054* | (2022.01) |
| *B22F 1/102* | (2022.01) |
| *B22F 1/17* | (2022.01) |
| *B22F 9/16* | (2006.01) |
| *B22F 9/24* | (2006.01) |
| *C30B 29/02* | (2006.01) |
| *C30B 29/52* | (2006.01) |
| *G01N 33/543* | (2006.01) |
| *B82Y 5/00* | (2011.01) |
| *B82Y 30/00* | (2011.01) |
| *B82Y 40/00* | (2011.01) |

(52) U.S. Cl.
CPC .......... *B22F 9/24* (2013.01); *A61K 49/0021* (2013.01); *A61K 49/0093* (2013.01); *A61K 51/1251* (2013.01); *B22F 1/054* (2022.01); *B22F 1/056* (2022.01); *B22F 1/102* (2022.01); *B22F 1/17* (2022.01); *B22F 9/16* (2013.01); *C30B 29/02* (2013.01); *C30B 29/52* (2013.01); *G01N 33/5434* (2013.01); *G01N 33/54346* (2013.01); *B22F 2301/255* (2013.01); *B22F 2301/30* (2013.01); *B22F 2301/40* (2013.01); *B22F 2302/45* (2013.01); *B22F 2303/15* (2013.01); *B22F 2303/20* (2013.01); *B22F 2999/00* (2013.01); *B82Y 5/00* (2013.01); *B82Y 30/00* (2013.01); *B82Y 40/00* (2013.01)

(58) Field of Classification Search
CPC ............ A61K 49/0021; A61K 49/0093; A61K 51/1251; B22F 1/054; B22F 1/102; B22F 1/17; B22F 9/16; B22F 2301/255; B22F 2301/30; B22F 2301/40; B22F 2302/45; B22F 2999/00; C30B 29/02; C30B 29/52; G01N 33/5434; G01N 33/54346; B82Y 5/00; B82Y 30/00; B82Y 40/00
See application file for complete search history.

(56) References Cited

U.S. PATENT DOCUMENTS

| | | | | |
|---|---|---|---|---|
| 5,075,426 A | * | 12/1991 | Zielinski | C07F 17/00 534/15 |
| 2009/0272913 A1 | | 11/2009 | Naciri et al. | |
| 2013/0058870 A1 | | 3/2013 | Lacroix et al. | |

FOREIGN PATENT DOCUMENTS

| | | |
|---|---|---|
| CN | 107186210 A | 9/2017 |
| WO | 2005044224 A2 | 5/2005 |
| WO | 2016139591 A1 | 9/2016 |
| WO | 2017053312 A1 | 3/2017 |
| WO | 2017173054 A1 | 10/2017 |

OTHER PUBLICATIONS

Search Report dated Feb. 25, 2019 for International Patent Application No. PCT.US2018/057134.4 (4 pages).
Written Opinion dated Feb. 25, 2019 for International Patent Application No. PCT.US2018/057134.4 (8 pages).

* cited by examiner

*Primary Examiner* — Robert S Cabral
(74) *Attorney, Agent, or Firm* — CHRISTENSEN O'CONNOR JOHNSON KINDNESS PLLC

(57) ABSTRACT

Nanoparticles, nanoparticle conjugates, devices for making nanoparticles and nanoparticle conjugates, and related methods of use and synthesis are described.

20 Claims, 30 Drawing Sheets

(Reaction 1)

(Reaction 2)

= NAKED (d) Cas-9 OR OTHER ENDONUCLEASE
= REDUCING AGENT
= MULTI-METAL NANOPARTICLE
= GUIDE-RNA
= NUCLEIC ACID MOLECULES
= MAGNET

▨ = NAKED (d) Cas-9 OR OTHER ENDONUCLEASE
✦ = REDUCING AGENT
⬡ = MULTI-METAL NANOPARTICLE
↩ = GUIDE-RNA
∥ = NUCLEIC ACID MOLECULES
⌒ = MAGNET

▭ = NAKED (d) Cas-9 OR OTHER ENDONUCLEASE
❊ = REDUCING AGENT
⬡ = MULTI-METAL NANOPARTICLE
∫ = GUIDE-RNA
║ = NUCLEIC ACID MOLECULES
⌒ = MAGNET

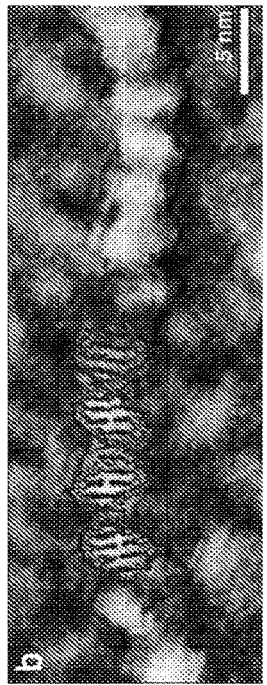
FIG. 17B
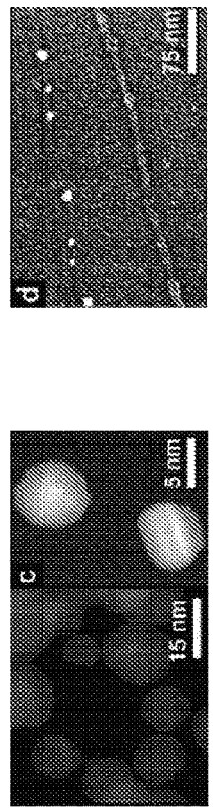
FIG. 17D
FIG. 17C
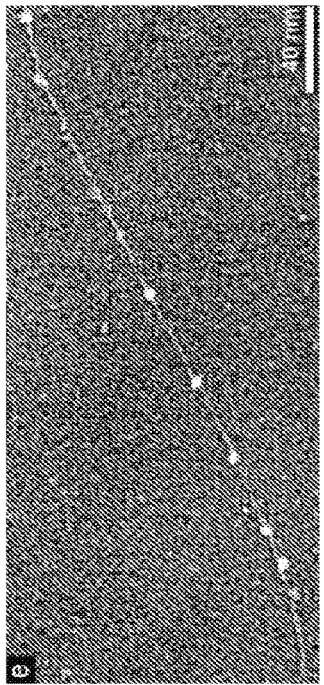
FIG. 17E
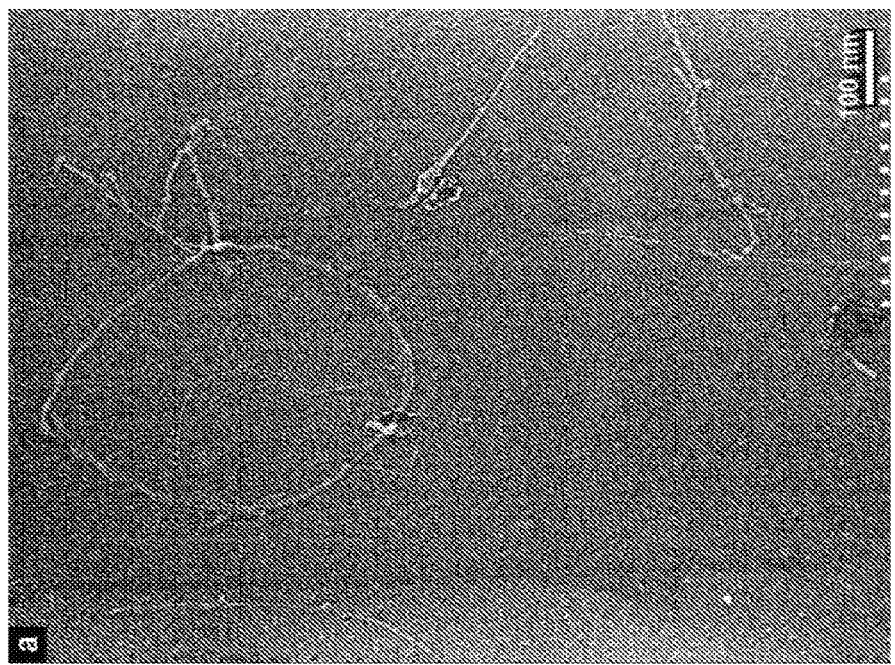
FIG. 17A

SINGLE- AND MIXED-METAL NANOPARTICLES, NANOPARTICLE CONJUGATES, DEVICES FOR MAKING NANOPARTICLES, AND RELATED METHODS OF USE

CROSS-REFERENCE(S) TO RELATED APPLICATION(S)

This application claims the benefit of priority from U.S. Nonprovisional patent application Ser. No. 16/758,770 filed Apr. 23, 2020, which claims the benefit of priority from International Patent Application No. PCT/US2018/057134 filed Oct. 23, 2018, which further claims the benefit of priority from U.S. Provisional Patent Application No. 62/576,009 filed Oct. 23, 2017, the disclosures of which are incorporated herein by reference in their entirety.

BACKGROUND

Many current solution-phase, single- and mixed-metal nanoparticle production protocols are based on seed-mediated, "bottom-up" self-assembly of sub-nanometer metal building blocks. The mechanisms governing seed-mediated growth of gold nanoparticles in solution phase at standard ambient temperature and pressure (SATP) are thought dependent on two pathways: kinetic controls and selective surface passivation. The latter matches various combinations of reductants and surfactants with specific metal chemistry and ion concentration. Development of various protocols based on these principles has expedited development of directed synthesis of monometallic nanoparticles. Given the different physico-chemical properties of multiple metals, e.g., finding matching surfactants and suitable reaction environments that work in concert, producing metal nanoparticles with well-defined morphology and composition is, however, disproportionately challenging.

In conventional, i.e. SATP, solution-phase reaction environments, trace elements, solvated gasses, volatile compounds, and potentially reactive micro-contaminants are already present or enter as ambient contamination. Residual polymers and surfactants are found in and on nanoparticles synthesized via this path; their synthetic role is difficult to define and post-production removal often difficult, if not impossible. They typically remain unidentified in reactions carried out at SATP. Given that even the most seemingly innocuous micro-contaminants influence nucleation and growth, i.e., below ppm concentration, a contaminant-free system is important for production of crystalline metal nanoparticles. Surfactant- and contaminant-free metal nanoparticle sols are needed for the increased demand from combined targeted imaging and therapeutic applications.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure provides a nanoparticle comprising a solid metal core that is free or substantially free of ligands or non-metallic bonds. In an embodiment, the nanoparticles described herein further include an organic shell coupled to an outer surface of the solid metal core.

In another aspect, the present disclosure provides a method for making metal nanoparticles that have a solid metal core that is free or substantially free of ligands and non-metallic bonds.

In another aspect, the present disclosure provides device for low-pressure, solution-phase synthesis of metal nanoparticles. In an embodiment, the device includes a single Schlenk line assembly; and an all-glass chemical reaction environment coupled to the single Schlenk line assembly including: a vacuum-stopped back pressure overload valve; a plurality of back pressure-loaded injectors; and a reaction vessel. In an embodiment, the device further includes a manometer-gated, tri-valved high-vacuum interface coupled to the single Schlenk line.

In another aspect, the present disclosure provides a method of tagging a target nucleic acid substrate with a nanoparticle as described further herein, comprising assembling a targeted nanoparticle construct on the target nucleic acid substrate, and a targeting moiety coupled thereto, wherein the targeting moiety selectively binds to a sequence in the target nucleic acid substrate.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

FIG. 17A is an ultra-high resolution scanning-electron microscope (UHRSEM) image of a nanoparticle, in accordance with an embodiment of the disclosure, coupled to an EcoR1 restriction enzyme attached to a PBR 322 E. coli plasmid undergoing rolling circle replication;

FIG. 17B is an electron microscopy image of a cryobiology sample preparation and modified application of special high-resolution imaging techniques with a DNA model overlayed on the electron microscopy image;

FIG. 17C includes images of gold (left) and iron (right) nanoparticles, in accordance with an embodiment of the disclosure;

FIGS. 17D and 17E are an electron microscopy images of gold nanoparticles coupled to restriction enzymes BamHI (FIG. 17D) and EcoR1 (FIG. 17E), in accordance with an embodiment of the disclosure.

DETAILED DESCRIPTION

Figure 1:
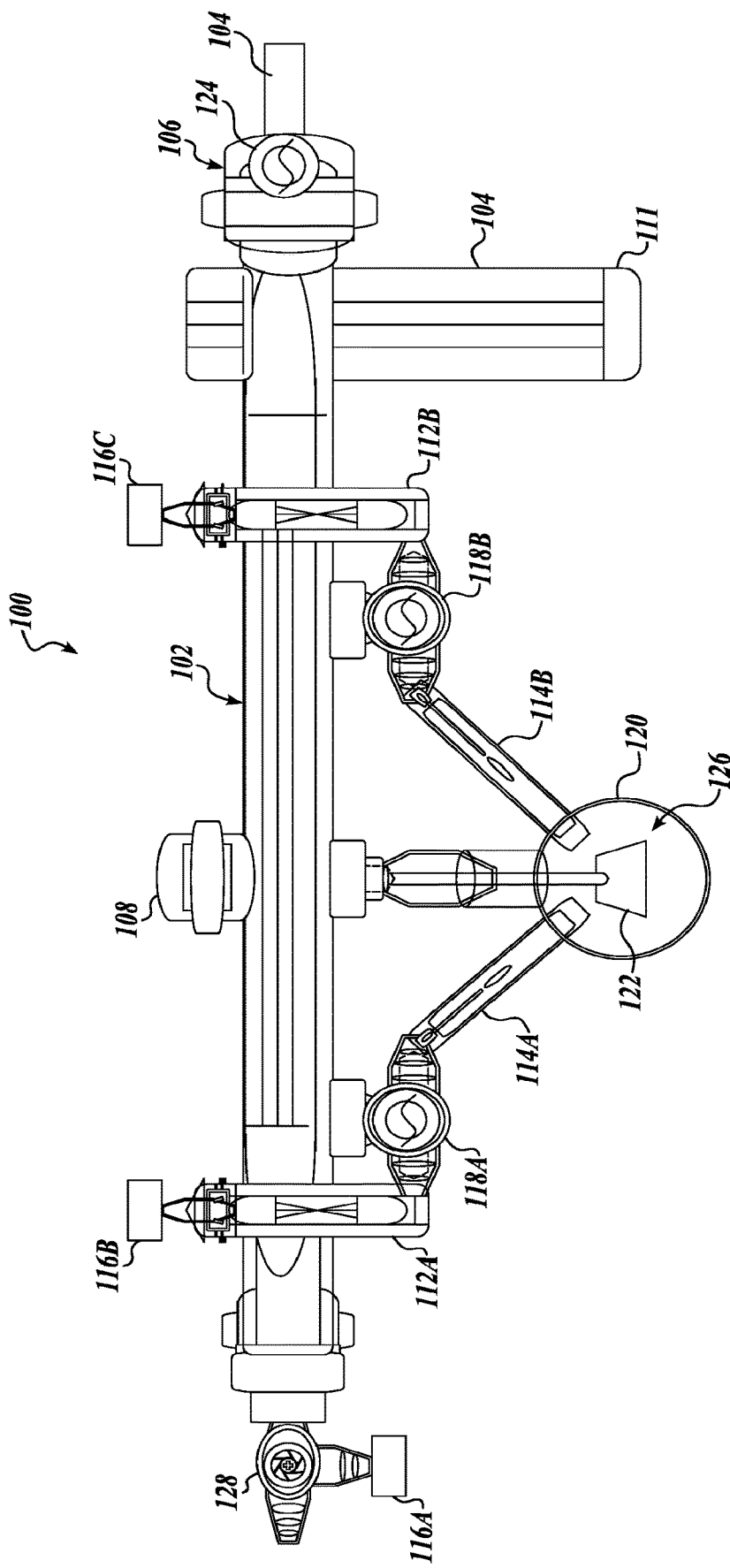
FIG. 1 is a schematic illustration of a device for low-pressure, solution-phase synthesis of metal nanoparticles, in accordance with an embodiment of the disclosure.

Nanoparticles, nanoparticle conjugates, devices for making nanoparticles and nanoparticle conjugates, and related methods of use are described.

Nanoparticles

In one aspect, the present disclosure provides a nanoparticle including a solid metal core free or substantially free of ligands and non-metallic bonds. The absence or substantial absence can be verified by mass spectral analysis, such as, gas chromatography-mass spectrometry, inductively coupled plasma-mass spectroscopy, and the like.

The core of the nanoparticles described herein is a solid metal core. In an embodiment, the solid metal core comprises a metal chosen from an alkali metal, an alkaline earth metal, a transition metal, a post-transition metal, a lanthanide metal, an actinide metal, and a metalloid. In an embodiment, the solid metal core comprises a plurality of metal atoms of a single element. In an embodiment, the solid metal core is a mixed metal core comprising two or more metal elements. In an embodiment, the mixed metal core has a predetermined ratio of components, dependent upon, for example, reaction conditions used in their synthesis.

In an embodiment, the nanoparticles described herein have a well-defined polyhedral geometry (in the sense that they are essentially free of or free of lattice defects). The absence or substantial absence of lattice defects can be verified by, for example, high-resolution scanning tunneling electron microscopy. In an embodiment, the nanoparticles described herein have essentially no or no surface ligands that are bound to a surface of the solid metal core. As described further herein with respect to the methods and devices of the present disclosure, in an embodiment, the nanoparticles are synthesized in reactions free or substantially free of surfactants, trace elements, solvated gasses, volatile compounds and potentially reactive micro-contaminants. The absence or substantial absence of surfactants, trace elements, solvated gases, volatile compounds, and potentially reactive micro-contaminants can be verified by mass spectral analysis, such as, gas chromatography-mass spectrometry, inductively coupled plasma-mass spectroscopy, and the like. Accordingly, in an embodiment, the nanoparticles are free of such contaminants. Further, in an embodiment, the solid metal core does not include non-metallic elements. In this regard, the solid metal core does not include non-metallic bridges between metal atoms disposed in the solid metal core.

In an embodiment, the nanoparticles described herein have a diameter in a range of about 0.5 nm to about 1000 nm. In an embodiment, the nanoparticles described herein have a diameter in a range of about 2 nm to about 200 nm. In an embodiment, the nanoparticles described herein have a diameter in a range of about 4 nm to about 100 nm.

In an embodiment, the nanoparticles described herein may be characterized by their three-dimensional geometry or shape. In an embodiment, the nanoparticles have a polyhedral shape. In an embodiment, the polyhedral shape includes Platonic solids, such as pyramids, and including Bravais-lattices face-centered cubic (FCC), hexagonal close packed (HCP), and body-centered cubic (BCC). In an embodiment, the nanoparticles described herein are supra-atomic crystalline materials exhibiting a Bravais-lattice selected from the group consisting of FCC, HCP and BCC. In an embodiment, the nanoparticles described herein have structure selected from the group consisting of possess a tetragonal, pyramidal, and hexagonal pyramidal structure.

In an embodiment, the nanoparticles described herein are electron-dense. Electron density of the nanoparticles of the present disclosure can be measured by back-scattered electrons scattered off of the nanoparticles. In an embodiment, the nanoparticles described herein are not hollow and/or electron-dense.

The solid metal core can have any number of physical characteristics. In an embodiment, one or more of elements of the solid metal core is radioactive. In an embodiment, the radioactive element is chosen from a radio-isotope of gold, indium, gadolinium, and platinum. In an embodiment, the solid metal core includes isotopes of alkali, alkaline earth, post-transition, transition, and lanthanide metals. In this regard, the nanoparticle is capable of delivering a radio-isotopic payload to a target tissue or cell. Likewise, such a radioactive nanoparticle can be used, for example, for labelling or imaging of a sample. In an embodiment, the solid metal core includes a stable isotope of iron, silver, or gold.

A number of such radioactive nanoparticles are illustrated in FIG. 3. The illustrated embodiments include Au @$^{111}$In, Au@$^{68}$Ga, and $_{197}$Au@$^{198}$Au Nanoparticles. FIG. 3A is a high-resolution electron micrograph of 5 nm gold$^{198}$ [Beta particle emitter] radioisotope core surrounded by stable gold$^{197}$. X-Ray Dispersive Spectroscopy [XRDS] analysis of particles is seen in FIG. 3D. FIG. 3B [Au@$^{111}$In] and 3C show high-resolution electron micrographs of Indium$^{111}$ [Gamma particle emitter] surrounded by a stable gold shell and Au@$^{68}$Ga nanoparticles, respectively. All samples were analyzed by XRDS or Electron Energy Loss Spectroscopy [EELS]. These techniques provide quantitative measurement of nanoparticle composition.

Figure 3C:
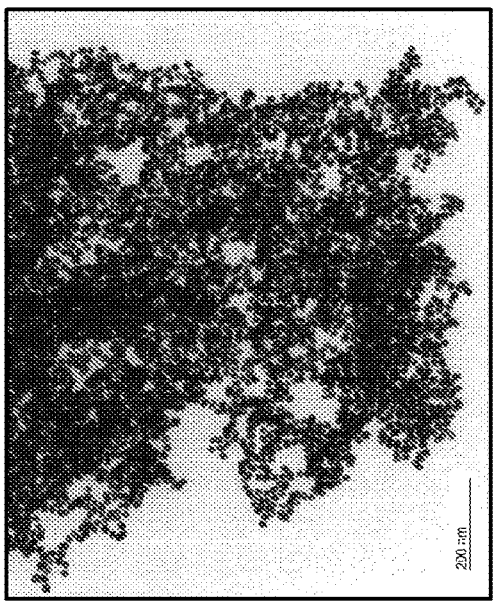
FIG. 3C is a high-resolution electron micrograph of a nanoparticle including a gold$^{68}$ core and a gadolinium shell, in accordance with an embodiment of the disclosure.
Figure 3B:
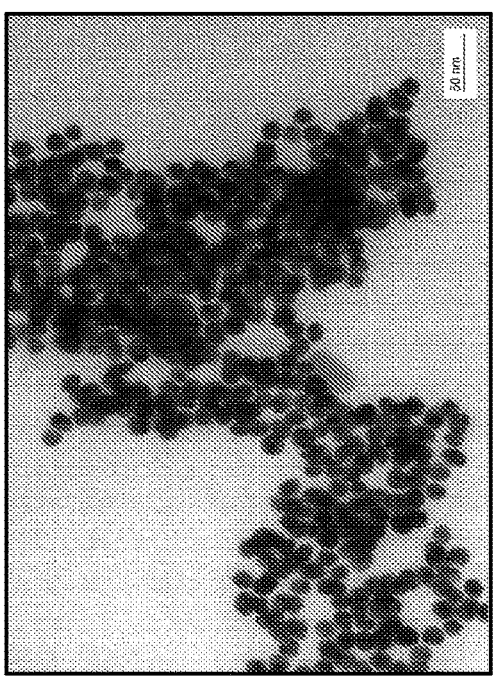
FIG. 3B is a high-resolution electron micrograph of a nanoparticle including an indium$^{111}$ core (Gamma particle emitter) surrounded by stable gold shell; in accordance with an embodiment of the disclosure.

Such nanoparticles can be used, for example, targeted imaging, diagnostics, and cancer therapies. FIG. 4 graphically illustrates gamma activity and shows scintillation analysis (inset) of the particles described and illustrated in FIGS. 3A-3C. As shown, ultra-high yields and purity are clearly exhibited in the scintillation analysis of six synthetic runs of Au@$^{111}$In radioisotope nanoparticles (framed insert). Average purity and yields of raw (untreated) nanoparticles are greater than 95%. This is greater than the highest yield ever published.

In an embodiment, the solid metal core is magnetic. As discussed further herein with respect to the methods of the present disclosure, nanoparticles comprising such magnetic solid metal cores are capable being magnetophoresced or otherwise isolated from a solution or suspension. In this regard, they are suitable in concentrating a target from a complex mixture. In an embodiment, the solid metal core has a magnetic property chosen from ferromagnetism, paramagnetism, and super-paramagnetism. In an embodiment, the solid metal core comprises one or more magnetic elements chosen from cobalt, iron, nickel, manganese, europium, and combinations thereof.

As discussed further herein, in an embodiment, the magnetic nanoparticle further includes a targeting moiety and can be used to manipulate DNA and extract specific nucleic acid fragments for sequencing and or genetic manipulation. In a further embodiment, the targeted magnetic nanoparticle includes a luminescent intercalating/cutting platinum compound configured to increase its functional spectrum.

In an embodiment, the solid metal core is configured to generate one or more signals in response to absorbing or scattering electromagnetic radiation. In an embodiment, the solid metal core is fluorescent. In an embodiment, the solid metal core is luminescent. In an embodiment, the solid metal core generates a signal including a visible light signal in response to absorbing or scattering electromagnetic radiation. In an embodiment, the solid metal core includes a material selected from the group consisting of gold, silver, iron, platinum, europium, and combinations thereof.

In an embodiment, the nanoparticles described herein are configured to generate a detectable signal in response to absorbing or scattering radio-frequency electromagnetic radiation. In an embodiment, the nanoparticles described herein are configured to amplify or concentrate radio-frequency electromagnetic radiation. In an embodiment, the solid metal core includes a metal selected from the group consisting of iron, gold, and an alloy of platinum and silver. In this regard, the nanoparticles described herein are suitable as antennae to focus radio-frequency delivery onto a target, particularly when the nanoparticles are targeted to a particular tissue or cell, such as in cancer treatment.

In an embodiment, the nanoparticles described herein include an organic shell coupled to an outer surface of the solid metal core. In an embodiment, the organic shell is coupled directly to the solid metal core. In an embodiment, the organic shell fully covers or envelopes the solid metal core. In an embodiment, the organic shell partially covers the solid metal core. In an embodiment, there is no linker between the organic shell and the solid metal core. In an embodiment, the outer surface of the solid metal core has a zero valence state. In an embodiment, the outer surface of the solid metal core coupled to the organic shell does not include metal oxides.

In an embodiment, the nanoparticles described herein further include secondary shell coupled to an outer surface of the organic shell. In an embodiment, the secondary shell comprises one or more metals. In an embodiment, the secondary shell completely covers or envelopes the organic shell. In an embodiment, the nanoparticles described herein include tertiary, quaternary, and more shells disposed on or over the organic layer.

Figure 2A:
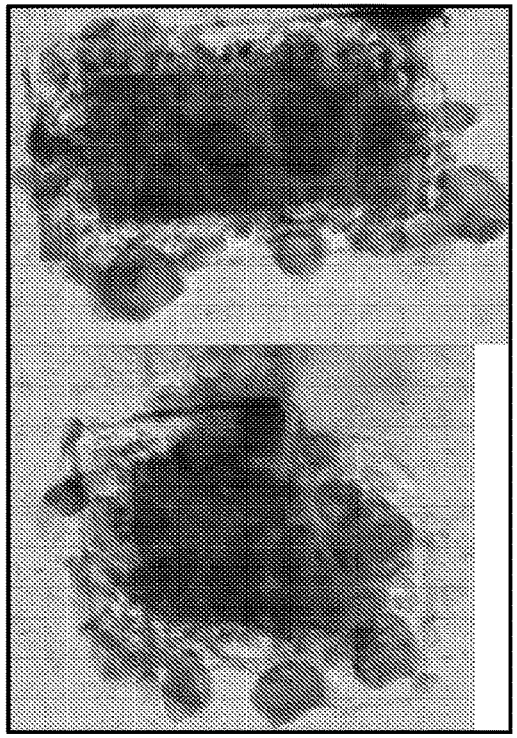
FIG. 2A is an image of a platinum gadolinium nanoparticles encased in Guar, in accordance with embodiments of the disclosure.

In an embodiment, the secondary shell includes a plurality of metal nanoparticles coupled to an outer surface of the organic shell. In the illustrated embodiment of FIG. 2A, the nanoparticle includes a solid metal core, in this case a cubic gadolinium core shown as the dark center of the nanoparticle, coupled to platinum nanoparticles through an organic shell. Such platinum (external 2 nm PtNPs) and gadolinium (cubic Gd cores) may be used as therapeutic and [PET/SPECT/MRI] biomedical imaging agents, respectively, and can be combined with stoichiometric precision into individual nanoparticles. Further, the nanoparticle includes an organic shell coupled to an outer surface of the solid metal core, shown here as the transparent layer disposed on the solid gadolinium core. Here the organic shell is Guar, an FDA-approved natural gum polymer.

Nanoparticle Conjugates

In an embodiment, the nanoparticles described herein include nanoparticle conjugates. In an embodiment, the organic shell includes an organic component coupled to the outer surface of the solid metal core chosen from a restriction enzyme, a protein, a carbohydrate, a lipid, an amino acid, a nucleic acid, and combinations thereof.

In an embodiment, the organic shell includes a targeting moiety configured to selectively bind to a target substrate. In an embodiment, the targeting moiety includes components chosen from one or more of an antibody, a functional antibody fragment or derivative, a TALENS, an aptamer, a restriction enzyme, a nucleic-acid guided endonuclease, an exonuclease, a polymerase, a nucleic acid modifying protein, an antibody, and combinations thereof. In an embodiment, the targeting moiety is chosen from Cas-9 and dCas-9. In an embodiment, the targeting moiety includes an endonuclease coupled to a guide nucleic acid, such as a guide RNA, configured to selectively bind to a target nucleic acid.

Figure 2B:
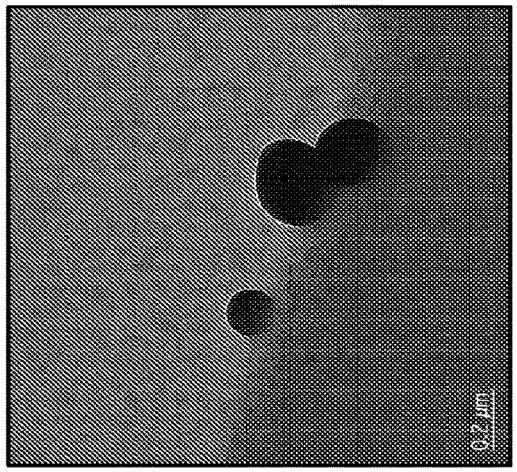
FIG. 2B is an image of iron gold nanoparticles encased in Zein, in accordance with an embodiment of the disclosure.

FIG. 2B is an image of iron gold composites encased in Zein. Zein is an FDA-approved natural corn protein. Pure Zein is clear, odorless and extremely stable and a candidate for use in adjuvant cancer therapies. Gold and iron are used as therapeutic (Au 198) and magnetic resonance imaging agents, respectively.

Figure 2C:
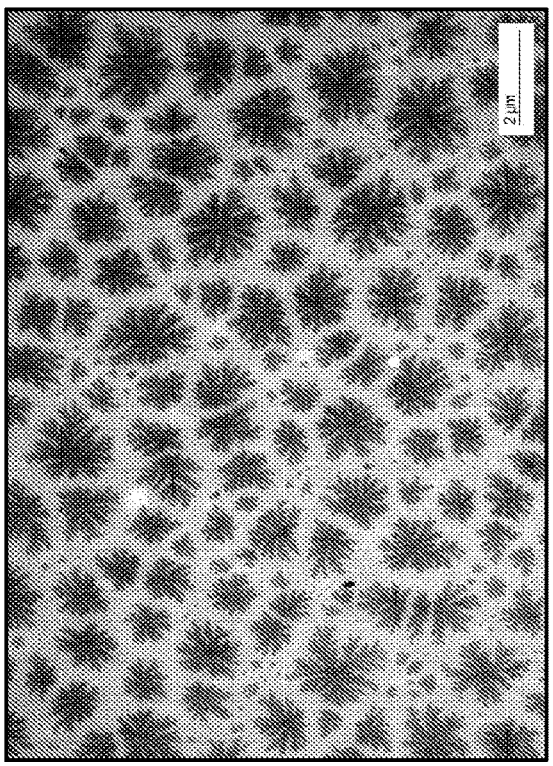
FIG. 2C in an image of platinum diethylene glycol composites, in accordance with embodiments of the disclosure.

FIG. 2C is an image of platinum di-ethylene glycol composites produced as an individual prototype to exhibit a novel self-assembly dendrimer protocol. Individual 2 nm nanoparticles self-assemble into large "snowflake" assemblies and can combine in a targeted complex with other metals within the diethylene glycol matrix.

Figure 16:
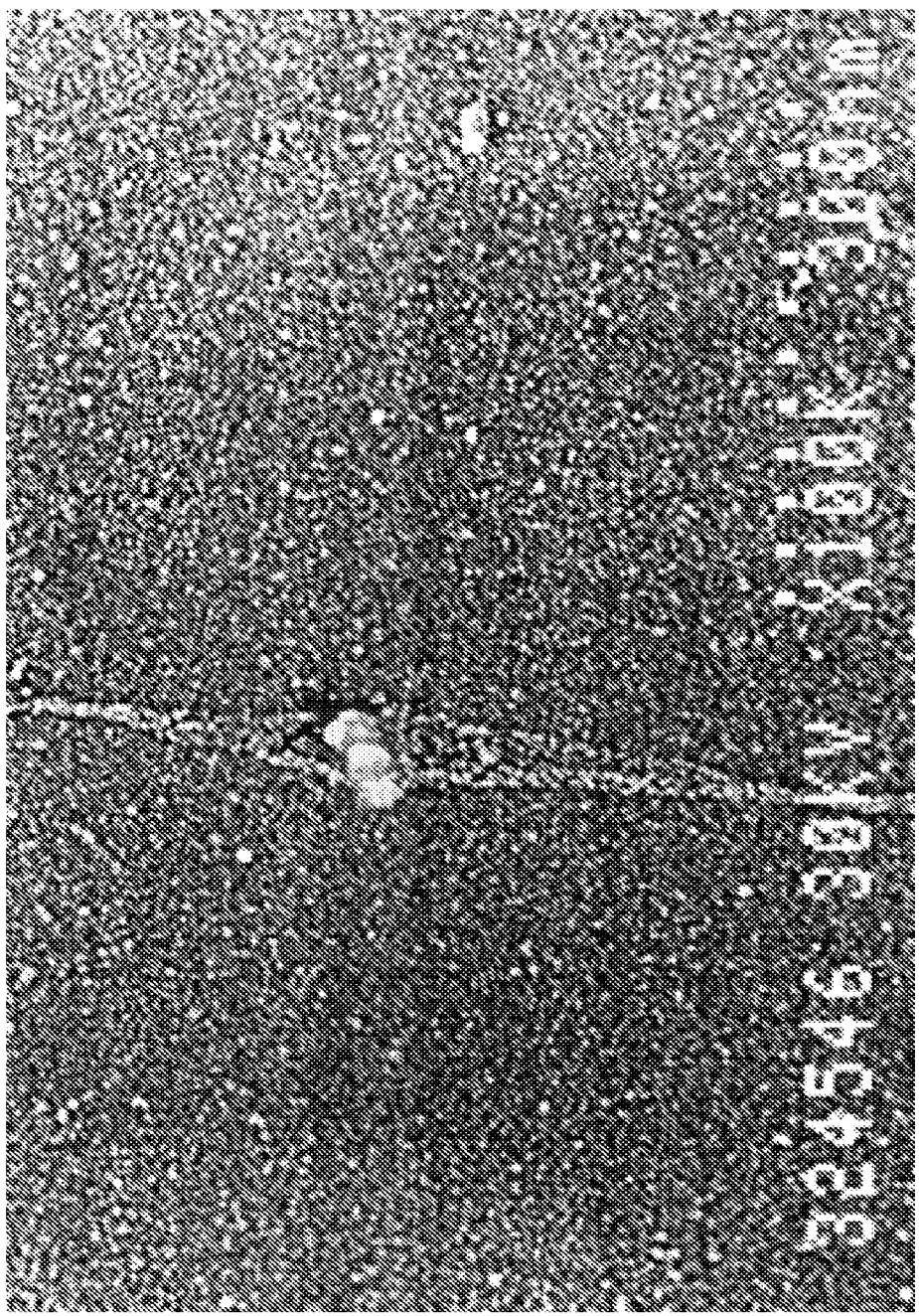
FIG. 16 is a high-resolution microscopy image of a topoisomerase unwinding duplex DNA labelled with a nanoparticle, in accordance with an embodiment of the disclosure.

In an embodiment, the organic shell includes a topoisomerase. In an embodiment, the topoisomerase is configured to selectively bind DNA. FIG. 16, illustrates a nanoparticle according to an embodiment of the disclosure including an iron solid metal core coupled to a topoisomerase bound to a target DNA. Restriction endonuclease/enzymes, topoisomerases and DNA-binding proteins were labelled with various metal nanoparticles and examined by high-resolution microscopy. Novel sample preparation and imaging techniques were developed out of exhaustive experimentation and led to the discovery of structural-functional interplay between nucleic acids, proteins and enzymes.

In an embodiment, the organic shell includes a restriction enzyme. In an embodiment, the restriction enzyme is configured to selectively bind to DNA. FIG. 17A illustrates a nanoparticle conjugate, according to an embodiment of the disclosure, including a gold solid metal core coupled to an endonuclease. As shown, the nanoparticle conjugate is shown facilitating rolling circle nucleic acid replication and bound to a target nucleic acid molecule.

In an embodiment, the organic shell includes an endonuclease. FIGS. 17D and 17E illustrate nanoparticle conjugates that include a restriction enzyme in the organic shell bound to target nucleic acid molecules, in accordance with embodiments of the present disclosure.

Figure 18:
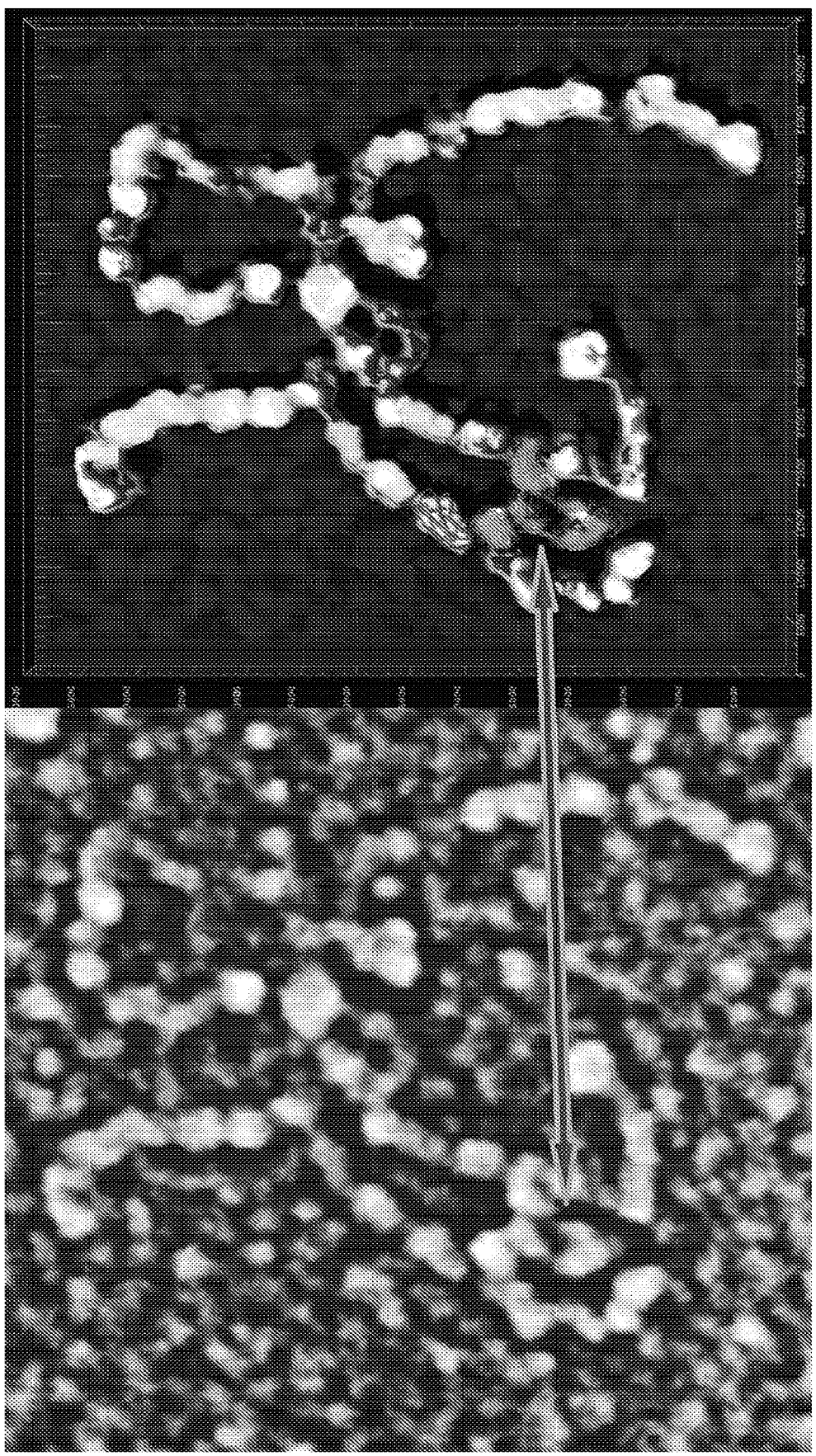
FIG. 18 (left) is a UHRSEM image of Tenascin (TNCN) labelled with IgGs coupled to gold nanoparticles, in accordance with an embodiment of the disclosure, and (right) a three-dimensional model of the nanoparticle-labelled IgG bound to TNCN.

In an embodiment, the organic shell includes an antibody, such as a monoclonal antibody. FIG. 18 illustrates a nanoparticle conjugate, in accordance with an embodiment of the disclosure, including a gold solid metal core coupled to an IgG. On the left is an ultra-high resolution scanning electron micrograph (UHRSEM) image, on the right a volumetric reconstruction incorporating molecular PDB structures into the model. Tenascin is a multi-armed glycoprotein active in developmental and remodeling events in vivo. A monoclonal antibody (arrow to Y-shaped IgG) was raised against the seventh FN (fibronectin) type 3. It can be seen bridging two arms of the spider-like macromolecule. Backscattered electron (BSE) signal detection of the 1 nm gold colloid (dot at base of Fe region of IgG) specifically localized the metal complex. The image was acquired in a custom Hitachi S900/S5000 UHRSEM microscope.

Figure 10A:
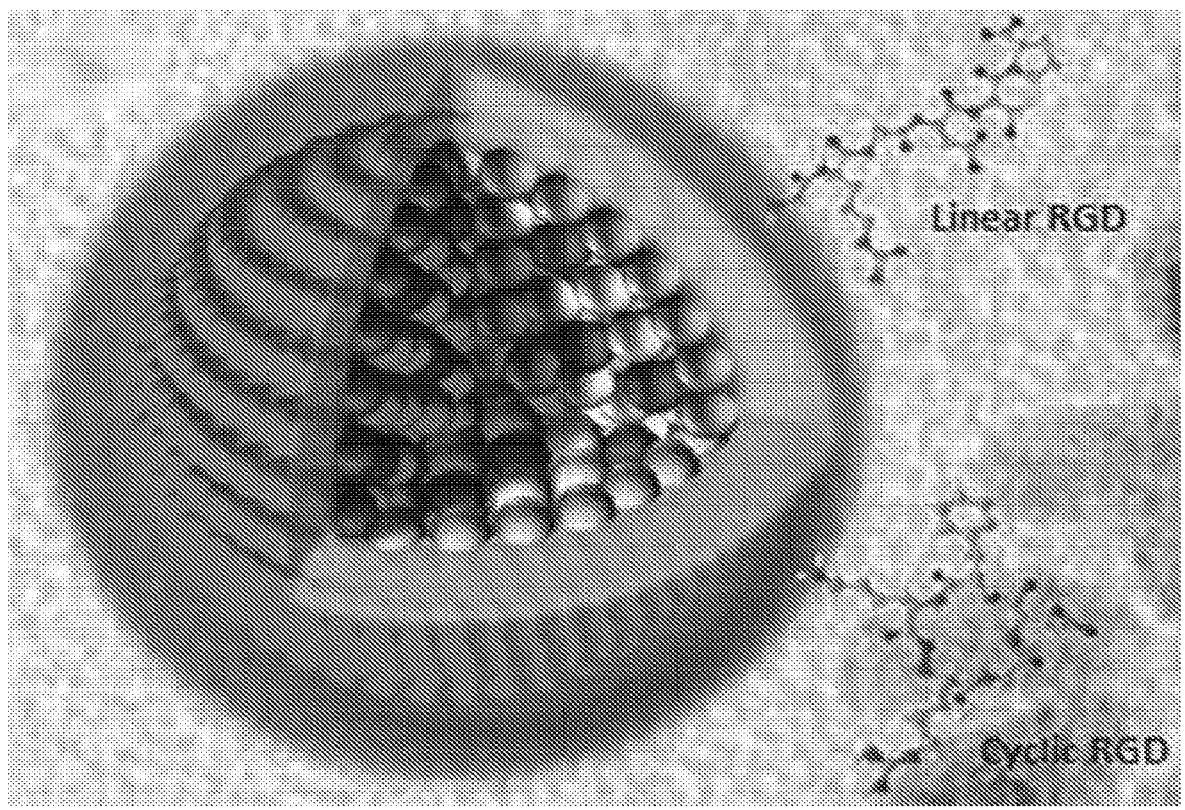
FIG. 10A is an illustration of a nanoparticle, in accordance with an embodiment of the disclosure, including an indium-111 labeled gold core modified with the tumor targeting peptide sequences arginine-glycine-aspartate (RGD) including cyclic and linear RGD sequences.

In an embodiment, the targeting moiety includes an RGD peptide. In an embodiment, the RGD peptide is a linear RGD peptide. In an embodiment, the RGD peptide is a cyclic RGD peptide. Embodiments of a nanoparticle according to the present disclosure including an RGD peptide are illustrated in FIG. 10A.

In an embodiment, the organic shell includes an anti-oxidant component. In a further embodiment, the nanoparticle including the anti-oxidant component further includes a targeting moiety, as discussed further herein, configured to selectively bind to a target. In this regard, in such an embodiment the targeted anti-oxidant particle can be used to selectively bind to, image, and destroy diseased cells, such as cancer cells.

Device for Making Nanoparticles and Nanoparticle Conjugates

Conventional solution-phase manufacture of single- and mixed-metal nanoparticles, core-shell nanoparticles, polymer and polymer-encapsulated metal nanoparticles is currently carried out under aerobic or inert atmospheres. Solution-phase nanoparticle synthesis under low or partial-pressure atmospheres has been described. Anoxic metal nanoparticle synthesis generally prevents metal-oxygen-metal bonding ("MOM") bridges and generally favors metal-metal bond formation. However, conventional protocols and equipment do not permit in-line synthesis, surface derivatization, and conjugation of such nanoparticles under constant partial pressure and under inert atmosphere.

Specifically, certain previous devices used for low-pressure, solution-phase synthesis of single- and mixed-metal nanoparticles included vapor-phase ballasts. In low-pressure, solution-phase chemistry, reactants may be suspended in a low-pressure "fog" at or below ambient temperature. Regulation of equilibrated vacuum levels between vapor-phase ballasts and the reaction environment is needed to establish and maintain a solution-vapor phase equilibrium between the reaction vessel and the ballasts. This has been referred to as an external "extended headspace". Previous designs using vapor-phase ballasts required an additional set of high-vacuum glassware ballasts; replenishing their liquid contents, continuous monitoring, and measuring and adjusting vacuum levels between ballasts and reaction vessels in-real time. This involved human intervention since complete automation of this process was not possible. Additional adjunct elements were also needed including, for example, a second Schlenk line and, thus, additional liquid nitrogen traps and gated manometers bridging vapor-phase ballasts to the reaction vessel. Those designs including vapor-phase ballasts provided surfaces separate from the reaction vessel onto which reactants condense. This involved disassembly and exhaustive cleaning of the entire Schlenk line(s) prior to successive reactions, polymer or metal shell deposition and/or conjugations.

To better meet this challenge, in an aspect the present disclosure provides a device for making, for example, the nanoparticles described herein. In an embodiment, the device includes a high-vacuum, all-glass reaction environment. A high-vacuum, all-glass environment provides good conditions for solution-phase syntheses of metal nanoparticles, because it can be cleaned with, for example, hydrofluoric acid to remove trace elements prior to high vacuum-evacuation of volatile compounds. To establish and maintain a suitable reaction environment for solution-phase growth of crystalline nanoparticles at reduced pressure, liquid-vapor boundary cryotechnology was combined with cleanroom and fabrication technology drawn from the semiconductor industry.

Accordingly, in an embodiment, the device includes a low-pressure, solution-phase single Schlenk line. In that regard, attention is directed to FIG. 1 in which a device 100, in accordance with an embodiment of the disclosure, is illustrated. As discussed further herein, the device 100 is suitable for injection of exact volumes of reactants under inert atmosphere at constant pressure, as well as independent control and monitoring of local vapor phase throughout the device 100. In the illustrated embodiment, the device 100 includes an ultra-high-vacuum single manifold Schlenk line 102 and an in-line series of manometer-gated valves 112A and 112B to establish and maintain strict kinetic/environmental controls of a solution-phase reaction at reduced pressure. Trace contaminants may be removed by cleaning glass surfaces of the device 100 with, for example, hydrofluoric acid. Volatile compounds subsequently removed by evacuation below the partial pressure of potentially solved gasses.

High-vacuum and solution-phase chemistry are in principle incompatible. Accordingly, in an embodiment, the device 100 includes a manometer-gated, tri-valved high-vacuum interface 106 coupled to the single Schlenk line 102 configured to provide an extended headspace maintained under low-pressure to establish a vapor-phase gradient in the reaction environment 126. In an embodiment, the device 100 for low-pressure, solution-phase synthesis of metal nanoparticles includes a single Schlenk line assembly 102; and an all-glass chemical reaction environment 126 coupled to the single Schlenk line assembly 102. In an embodiment, the all-glass chemical reaction environment 126 coupled to the single Schlenk line assembly 102 includes one or more vacuum-stopped back-pressure overload valves 112A and 112B; a plurality of back pressure-loaded injectors 114A and 114B; and a reaction vessel 120.

In an embodiment, the manometer-gated, tri-valved high-vacuum interface 106 is configured to establish and maintain a consistent and precise vacuum level within the single Schlenk line 102. Constant low pressure may be maintained by a wet/dry turbo-molecular pumping system (HVAC). Pressure gated isolation of individual environments may be balanced through the tri-valved gate 106 in concert with vacuum-stopped back-pressure overload valves 112A and 112B and back-pressure-loaded injectors 114A and 114B. In an embodiment, the manometer-gated, tri-valved high-vacuum interface 106 is in selective fluidic communication with a source of noble gas, such as noble gas sources 116A-116C, and a vacuum 104; and further comprises a manometer-gated switch 124 configured to selectively place the single Schlenk line 102 in fluid communication with one of the sources of noble gas 116A-116C and the vacuum 124. In this regard, the manometer-gated, tri-valved high-vacuum interface 106 is configured to balance pressure at the vapor-phase by using the gated-manometer 124 to switch between vacuum 104 and noble gas sources 116A-116C routed through the single Schlenk line 102 and its components without the use of an external "headspace" that was established with bridged vapor phase ballasts as in previous instruments, e.g., dual Schlenk line devices. Accordingly, in an embodiment, the device does not include a vapor-phase ballast.

As illustrated in FIG. 1, in an embodiment, the single Schlenk line 102 includes a first end coupled to a source of a noble gas 116A, such as argon, nitrogen, and/or hydrogen, through a valve 128. In an embodiment, and as discussed above, the single Schlenk line 102 has a second end opposite the first end coupled to the tri-valved high-vacuum interface 106. Further, in an embodiment, the reaction vessel 120 is coupled to the single Schlenk line 102 through one or more unbridged manometer-gated, vacuum-stopped, back-pressure overload (VSBPO) valves each including a gated manometer 118A and 118B and a vacuum-stopped, back pressure overload valve 112A and 112B. Further, in an embodiment, the reaction environment 126 includes a round-bottom flask 120 and a magnetically coupled glass rotor 122 disposed within the round-bottom flask 120, wherein the glass rotor 122 is magnetically coupled to a magnetically-coupled rotor drive 108 configured to rotate the rotor 122 within the round-bottom flask 120. In an embodiment, the device 100 further includes a liquid nitrogen trap 110 in fluid communication with the single Schlenk line 102 and configured to condense gases in the single Schlenk line 102, such as with liquid nitrogen 111. As shown, the liquid nitrogen trap 110 is disposed in line. Repeated evacuation/purging, such as to pressures less than or equal to $10^{-2}$ Pa, with ultrapure noble gas removes residual gases, volatile compounds, and trace elements while maintaining a contaminant-free low-pressure environment prior to and during the reaction.

In an embodiment, one or more components of the reaction environment 126 are coupled to the single Schlenk line by one or more ultra-high vacuum-sealed joints, such as gated manometers 118A and 118B.

The devices 100 described herein permit in-line, sequential layering of composite (organic and/or polymer) shells and deposition/fixation of secondary nanoparticles. This process can be further augmented for rapid, scalable nanocomposite production; including conjugation of targeting molecules (e.g., IgGs), signal-generating moieties (fluorophores, radioisotopes) as well as visible (e.g., color-coded materials) and their encapsulation into organic shells (e.g., for advanced drug-delivery systems), without any modifications to the design. The single Schlenk-line design is configured for true sealed-system "daisy-chain" production of multiplexed nanoparticles. Such a device 100 conforms to current ISO/GLP/GMP medical and pharmaceutical standards and includes nanoparticles produced for diagnostic and therapeutic applications superseding existing ISO and GMP standards for biomedical research.

Methods for Using the Device to Make Nanoparticles and Nanoparticle Conjugates

In another aspect, the present disclosure provides a method for making the nanoparticles and nanoparticle conjugates described herein.

The methods described herein incorporate two (2) unbridged manometer-gated, VSBPO valves on a single Schlenk vacuum line. See for example, FIG. 1. As described further herein with respect to the devices of the present disclosure, such as device 100, the VSBPO valves are coupled to a manometer-gated, tri-valved high-vacuum interface leading to a) Schlenk line and b) back-pressure fed injectors that feed into the reaction environment. In this regard, the methods of the present disclosure are suitable for independent injection of reactants, affinity ligands and polymers at the vapor/liquid phase boundary under partial pressure and inert atmosphere. The process described herein permits sequential, in-line manufacture of nanoparticles and is scalable and capable of producing a continuous stream of nanoparticles, such as, without decoupling individual elements of the device. The methods of the present disclosure are also suitable for direct- and reverse-seeding of core-shell NPs under reduced-pressure transfer into secondary reaction environments. In an embodiment, seeding particles, secondary shells, or polymer envelopes are "sucked" into the reaction environment under back-pressure transfer. The methods of the present disclosure also permit back-and-forth transfer of reactants for deposition of multiple core/shell layers and conjugates. In an embodiment, individual vacuum lines can be "daisy chained" to increase sequential synthetic capabilities.

The configurations described herein further allow continuous layering of organic polymers and/or simultaneous conjugation of ligands, proteins or nucleic acids. Previously-described methods for low-pressure, solution-phase production of nanoparticles required a series of vapor-phase ballasts, where continuous injection required an interrupted batching process. In contrast, the methods described herein facilitate linear synthetic progressions, i.e., back-and-forth synthesis using a preliminary product that can act as a secondary physical platform. This can be through controlled deconstruction of one core-shell composite into another with the addition of secondary or tertiary reagents. For example, magnetic nanoparticle DNA composites can be separated into two moieties; the magnetic moiety separated and removed and the DNA/protein composite to be processed further.

Single Schlenk line synthesis, as described herein, permits in-line sequential layering of composite, such as organic shells, and deposition/fixation of secondary nanoparticles. This process can be further augmented for rapid scalable nano-composite production; including conjugation of targeting molecules (e.g., IgGs, signal generating moieties (fluorophores, radioisotopes), as well as visible (e.g., color-coded materials) and their encapsulation into organic envelopes (e.g., for advanced drug-delivery systems), without any modifications to the design. The single Schlenk design is suitable for true "daisy-chain" production of multiplexed nanoparticles.

Methods for Using Nanoparticle Conjugates

Nanoparticles such as those disclosed herein can be incorporated into a variety of applications, all of which are encompassed by the present disclosure. Inclusion of an appropriate targeting moiety with the nanoparticle provides a targeted nanoparticle construct that can selectively bind any target substrate of interest. In one embodiment, the targeting moiety is configured to specifically bind to a target nucleic acid sequence, which permits the nanoparticle tagging of a nucleic acid substrate that comprises the target nucleic acid sequence. This can be applied for a variety of applications, including use in targeted nucleic acid sequencing applications, identification and/or isolation of nucleic acids from any source organism or synthetic system and/or fragments thereof, sequencing-based assaying technologies in vitro and/or in vivo. Furthermore, the targeted nanoparticle conjugates can be used in imaging and diagnostics. For example, the targeted nanoparticle conjugates can be configured for use in commercial research and development, such flow and mass cytometry, microscopy, and spectroscopy applications.

Accordingly, in one embodiment the disclosure provides a method of tagging a target nucleic acid substrate with a nanoparticle. The method comprises assembling a targeted nanoparticle construct on the target nucleic acid substrate. The targeted nanoparticle construct comprises a nanoparticle, for example as described herein, and a targeting moiety coupled thereto. The targeting moiety selectively binds to a sequence in the target nucleic acid substrate.

The term "assembling a targeted nanoparticle construct" encompasses embodiments where the targeted nanoparticle construct is pre-assembled and is merely contacted to the target nucleic acid substrate. This pre-assembly can comprise coupling the nanoparticle to the nanoparticle targeting moiety or a precursor thereof and then contacting the targeted nanoparticle construct to the target nucleic acid substrate under conditions to permit selective binding of the targeting moiety to the sequence in the target nucleic acid substrate. See, e.g., the illustrative schematic representations of FIGS. 11A-11C and 12A-12C.

Figure 11A:
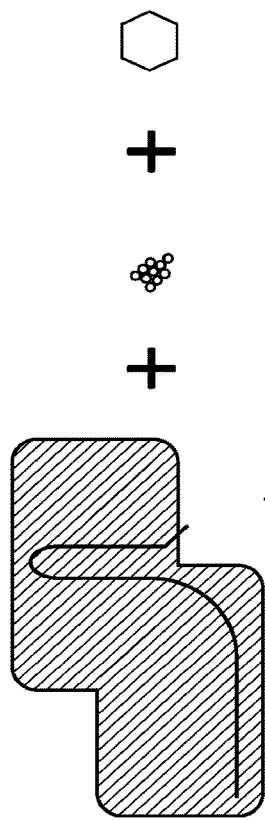
FIGS. 11A-11C schematically illustrate a method of tagging a target nucleic acid with a nanoparticle, in accordance with an embodiment of the disclosure.
Figure 11B:
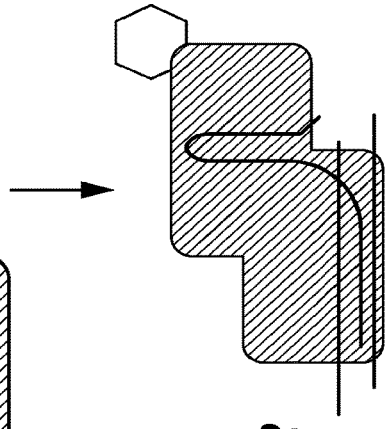
Figure 11C:
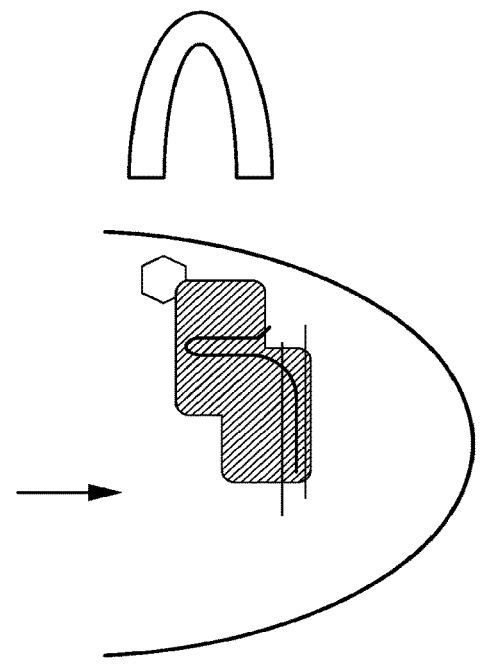

FIG. 11A illustrates a (d)Cas-9 endonuclease preloaded with a guide-RNA (gRNA) and conjugated to a multi-metal nanoparticle in the presence of a reducing agent. In FIG. 11B, the conjugate identifies its DNA target by the loaded gRNA. FIG. 11C illustrates an embodiment of purifying the target by immobilizing the magnetic nanoparticle conjugate with a magnet and washes are performed to remove residual non-specific DNA.

Figure 12A:
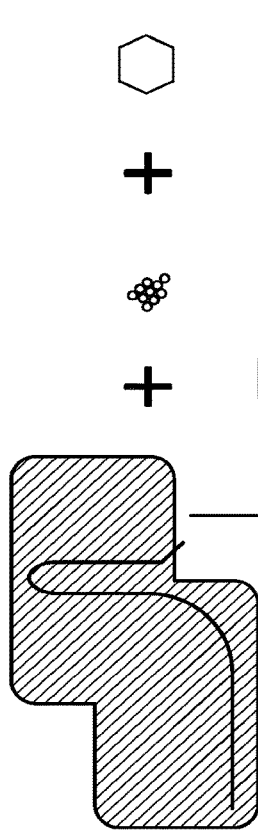
FIGS. 12A-12C schematically illustrate a method of tagging a target nucleic acid with a nanoparticle, in accordance with an embodiment of the disclosure.
Figure 12B:
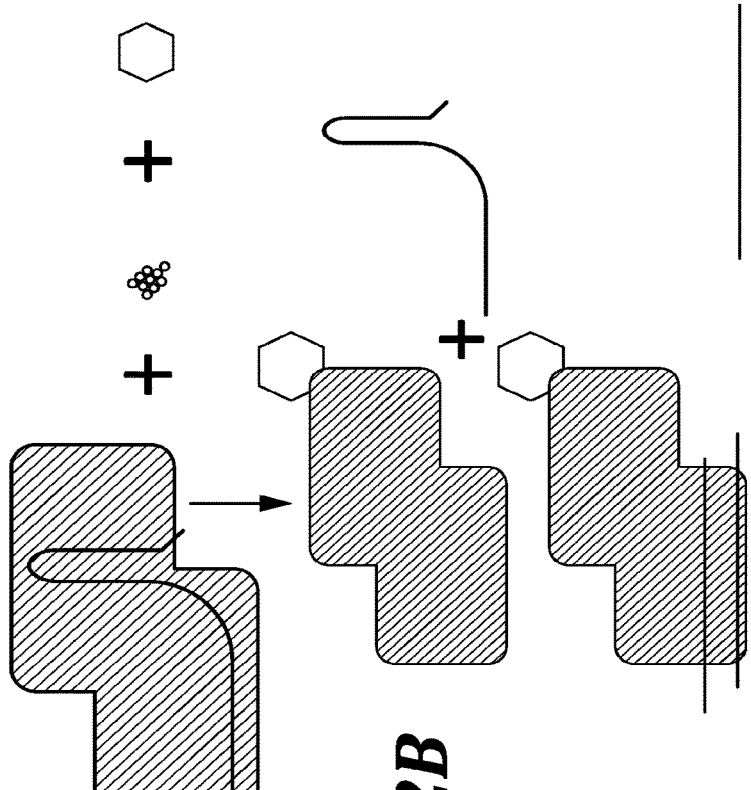
Figure 12C:
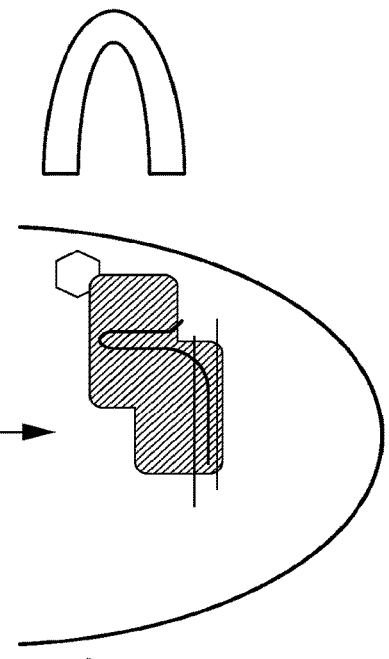

FIG. 12A illustrates an unloaded gRNA (d)Cas-9 endonuclease conjugated to a multi-metal nanoparticle in the presence of a reducing agent. In FIG. 12B, the conjugate is shown loaded with gRNA and in the same reaction finds its nucleic acid target or this can be performed in a second reaction. As in FIG. 11C, in FIG. 12C the target is shown purified by immobilizing the magnetic nanoparticle conjugate with a magnet and washes are performed to remove residual non-specific DNA.

Alternatively, the nanoparticle targeting moiety can be first contacted to the target nucleic acid substrate under conditions to permit selective binding of the targeting moiety to the sequence in the target nucleic acid substrate. Once bound, the nanoparticle can then be added and coupled to the targeting moiety already bound to the sequence in the target nucleic acid substrate. See, e.g., the illustrative schematic representation of FIGS. 13A-13C.

Figure 13A:
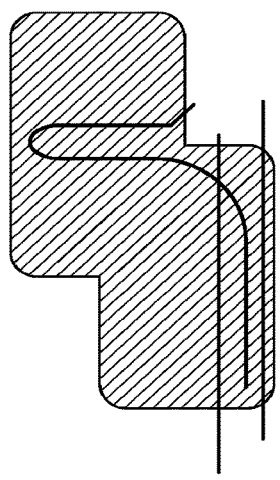
FIGS. 13A-13C schematically illustrate a method of tagging a target nucleic acid with a nanoparticle, in accordance with an embodiment of the disclosure.
Figure 13B:
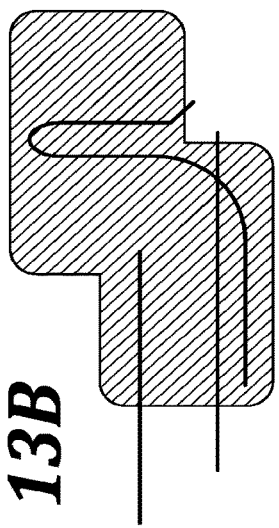
Figure 13C:
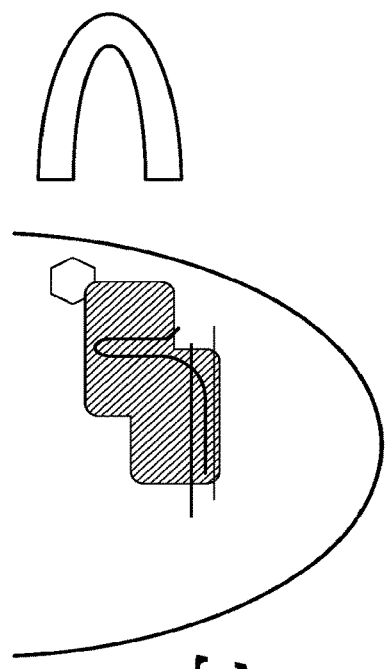

In FIG. 13A, (d)Cas-9 endonuclease is shown preloaded with a guide-RNA (gRNA) and identifies its nucleic acid target. The gRNA loading and target binding can be performed in a single reaction or in two reactions. In FIG. 13B, the loaded (d)Cas-9 is illustrated bound to its target is conjugated to a multi-metal nanoparticle in the presence of a reducing agent. In FIG. 13C, the target is shown purified by immobilizing the magnetic nanoparticle conjugate with a magnet and washes are performed to remove residual non-specific DNA.

Coupling of the nanoparticle to the targeting moiety can be accomplished using appropriate reducing agents. A non-limiting list of exemplary reducing agents useful to conjugate the nanoparticle and targeting moiety (e.g., DNA-interacting proteins such as Cas9) includes TCEP (tris(2-carboxyethyl)phosphine), EDC or EDAC (1-ethyl-3-(3-dimethylaminopropyl)carbodiimide hydrochloride), a metal, ADH, alcohol dehydrogenase, ascorbic acid, bis(pinacolato)

diboron, a borane, catecholborane, carrots, copper hydride, copper (low valent), chromium (low valent), *Daucus carota*, decaborane, DEMS, DIBAL-H, diborane, diethoxymethylsilane, diethyl 1,4-dihydro-2,6-dimethyl-3,5-pyridinedicarboxylate, diisobutylaluminium hydride, diisopropylaminoborane, 1,3-dimethylimidazol-2-ylidene borane, dimethylsulfide borane, DMSB, formaldehyde, formic acid, hantzsch ester, hydrazine, hydrogen, indium (low valent), iron, isopropanol, LAH, LiTEBH, lithium, lithium aluminum hydride, lithium tetrahydridoaluminate, lithium triethylborohydride, magnesium, manganese, mercaptoethylamine-HCl, 3-mercaptopropionic acid, 2-methylpyridine borane, 3-MPA, NBSH, neodymium (low valent), nickel, nickel borohydride, niobium (low valent), 2-nitrobenzenesulfonylhydrazide, phenylsilane, phosphorous acid, PICB, α-picoline-borane, pinacolborane, PMHS, polymethylhydrosiloxane, potassium, potassium borohydride, potassium iodide, potassium tetrahydroborate, 2-propanol, red-Al, rongalite, samarium (low valent), Schwartz's reagent, a silane, sodium, sodium bis(2-methoxyethoxy)aluminumhydride, sodium bisulfite, sodium borohydride, sodium cyanoborohydride, sodium dithionite, sodium hydrogensulfite, sodium hydrosulfite, sodium hydroxymethanesulfinate, sodium tetrahydroborate, sodium triacetoxyborohydride, strontium, sulfur, superhydride, tetramethyldisiloxane, a tin hydride, titanium (low valent), TMDSO, tributylstannane, tributyltin hydride, tributylphosphine, trichlorosilane, triethylphosphine, trimethylphoshpine, triphenylphosphine, triphenylphosphite, triethylsilane, tris(trimethylsilyl)silane, TTMSS, vasicine, vitamin C, zinc, and zirconocene chloride hydride.

Target Substrates

Target substrates generally comprise nucleic acids. As used herein, the term "nucleic acid" refers to any polymeric molecule that comprises multiple nucleotide subunits (i.e., a polynucleotide). Nucleic acids encompassed by the present disclosure can include deoxyribonucleotide polymer (DNA), ribonucleotide polymer (RNA), cDNA or a synthetic nucleic acid known in the art.

Nucleotide subunits of the nucleic acid polymers can be naturally occurring or artificial or modified. A nucleotide typically contains a nucleobase, a sugar, and at least one phosphate group. The nucleobase is typically heterocyclic. Canonical nucleobases include purines and pyrimidines and more specifically adenine (A), guanine (G), thymine (T) (or typically in RNA, uracil (U) instead of thymine (T)), and cytosine (C)). The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate, or triphosphate. These are generally referred to herein as nucleotides or nucleotide residues to indicate the subunit. Without specific identification, the general terms nucleotides, nucleotide residues, and the like, are not intended to imply any specific structure or identity. The nucleotides can also be synthetic or modified.

In some embodiments, the target substrates can include substrates comprising DNA. Such DNA-based substrates can have DNA that is derived from any relevant source, such as bacteria, archaea, eukaryotic microorganisms, single eukaryotic cells, synthetic organisms, organelles such as mitochondria, DNA viruses, transposable elements and other genomic elements, circulating tumor cells. The DNA substrates can be obtained from or derived from biological samples, such as bodily fluids and biopsies, or from cell-free DNA (cfDNA), treated samples. The DNA can be naturally derived or synthetic. The synthetic DNA can include PNAs and LNAs, and the like. The DNA substrate can be in processed or pre-treated samples, such as DNA that has been converted into a library or library pool for next generation sequencing, nucleic acid polymers. The target DNA substrate can be attached to a solid surface and/or further comprise additional non-DNA components. For example the DNA substrate can comprise the target DNA and a protein or peptide (including fusion a protein), an aptamer, a fusion protein, RNA, PNA, and the like. The treated sample can have the target DNA substrate preserved in situ, such as in formalin-fixed paraffin embedded (FFPE) tissue samples. Furthermore the target DNA substrate can comprise the target DNA sequence non-covalently bound (i.e., hybridized) to another nucleic acid molecule, such as DNA or RNA. The DNA can be produced by reverse transcription from an RNA template.

The DNA component of the target substrate can be of any appreciable size such that a targeting moiety can selectively bind to it. In some embodiments, the DNA component is at least 4 bases in length or more (e.g., up to a million bases or even more—there is no upper limit). The DNA can be linear, circular, branched, single stranded, partially or fully double stranded, and the like. The DNA component can have multiple domains, which are of known or unknown sequence, so long as there is sufficient known sequence and/or three-dimensional structure to permit the development of a targeting moiety to be configured to selectively bind to it. For example, a domain of unknown sequence can be flanked on one or both of the 5' end and 3' end with domains of known sequence. The 5' end and 3' end with domains of known sequence can be, for example, adaptor and/or barcode or tag sequences that facilitate capture, amplification, and/or sequencing, etc., using e.g., PCR, qPCR, next generation sequencing platforms, hybrid capture, hybridization chain reaction, and the like. Alternatively, a known sequence can be flanked on one or both of the 5' end and 3' end with domains of unknown sequence. In one illustrative example, a circular cloning plasmid with an insert may have multiple domains of known sequence that flank either end of an insert with unknown sequence. In any embodiment, the known or unknown domains can be DNA, or can alternatively be another nucleic acid such as RNA and/or PNA, as long as there is a known DNA sequence that is targeted by the targeting moiety for selective binding.

In other embodiments, the target substrates can include substrates comprising RNA. The target RNA can be derived from total RNA, mRNA, siRNA, microRNA, long non-coding RNA, and the like. Like DNA targets substrates, the target RNA substrates can have RNA that is derived from any relevant source, such as bacteria, archaea, eukaryotic microorganisms, single eukaryotic cells, synthetic organisms, organelles such as mitochondria, RNA viruses, circulating tumor cells. The RNA substrates can be obtained from or derived from biological samples, such as bodily fluids and biopsies, or from cell-free RNA (cfRNA), treated samples. The RNA substrate can be in processed or pre-treated samples, such as RNA that has been converted into a library or library pool for next generation sequencing, nucleic acid polymers. The target DNA substrate can be attached to a solid surface and/or further comprise additional non-DNA components. For example the DNA substrate can comprise the target DNA and a protein or peptide (including fusion a protein), an aptamer, a fusion protein, DNA, PNA, and the like. The treated sample can have the target RNA substrate preserved in situ, such as in formalin-fixed paraffin embedded (FFPE) tissue samples. Furthermore the target RNA substrate can comprise the target RNA sequence non-covalently bound (i.e., hybridized) to another nucleic acid molecule, such as RNA or DNA.

The description of the DNA component of DNA-containing substrates can be generally applicable to the RNA component of a substrates comprising RNA and are not repeated in their entirety. However, it is briefly noted that the RNA component can similarly be of any size and can contain various domains of known and unknown sequence in any configuration. There can also be domains of different nucleic acid types, such as The target nucleic acid substrates can be in any relevant biological sample, such as a fluid or solid sample obtained from a subject. Such fluid samples include blood, plasma, mucus, cerebral spinal fluid, and the like. Solid samples include biopsy samples. The target nucleic acid substrates can be in a prepared or processed sample (e.g., ultimately derived from a subject). For example, cells may have been grown ex vivo for some time and then processed to release the cellular DNA. Finally, solid tissue or cell samples can be processed and preserved to permit in situ applications for microscopic imaging. Such samples mentioned herein are for illustrative purposes only and other samples relevant for this disclosure are known in the art.

Targeting Moieties

The targeting moieties can be any molecule or molecule subassembly that can selectively target and bind a target substrate of interest with a specific affinity (i.e., detectable over background). As used herein, the term "selectively bind" means the ability to form a covalent or non-covalent interaction that the targeting moiety and target substrate form a complex under conditions where the targeting moiety does not interact and form complexes with off-target substrates (i.e., with divergent structures). Typically, the non-covalent interaction is sufficiently strong such that the complex has prolonged stability, e.g., to permit isolation and other manipulations.

In some embodiments, the targeting moiety is a nucleic acid-interacting protein. Illustrative, non-limiting examples of nucleic acid-interacting proteins useful as a targeting moiety include enzymatic proteins such as type II restriction enzymes, DNA/RNA modifying proteins, RNA/DNA guided endonucleases, endonucleases, exonucleases, fusion proteins, TALENS, antibodies and functional fragments or derivatives thereof, aptamers, peptides, and the like.

In some embodiments, the targeting moiety is an antibody. As used herein, the term "antibody" can refer to whole antibodies, but also encompasses antibody fragments and derivatives thereof, even if not explicitly indicated as such. The antibodies (and fragments or derivatives) can be obtained or derived from any antibody-producing mammal (e.g., mouse, rat, rabbit, and primate including human), that specifically bind to an antigen of interest. Exemplary antibodies include polyclonal, monoclonal and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies. The antigen-binding molecule can be any intact antibody molecule or fragment thereof (e.g., with a functional antigen-binding domain).

An antibody fragment is a portion derived from or related to a full-length antibody. A "functional" fragment typically refers to the maintenance of the ability to bind the target substrate. Thus, the antibody fragment preferably includes the complementarity-determining regions (CDRs), antigen binding regions, or variable regions thereof. Illustrative examples of antibody fragments useful in the present disclosure include Fab, Fab', F(ab)$_2$, F(ab')$_2$ and Fv fragments, scFv fragments, diabodies, linear antibodies, single-chain antibody molecules, multispecific antibodies formed from antibody fragments, and the like. A "single-chain Fv" or "scFv" antibody fragment comprises the $V_H$ and $V_L$ domains of an antibody, wherein these domains are present in a single polypeptide chain. The Fv polypeptide can further comprise a polypeptide linker between the $V_H$ and $V_L$ domains, which enables the scFv to form the desired structure for antigen binding. Antibody fragments can be produced recombinantly, or through enzymatic digestion.

Antibodies can be further modified to suit various uses. For example, a "chimeric antibody" is a recombinant protein that contains the variable domains and complementarity-determining regions (CDRs) derived from a non-human species (e.g., rodent) antibody, while the remainder of the antibody molecule is derived from a human antibody. A "humanized antibody" is a chimeric antibody that comprises a minimal sequence that conforms to specific complementarity-determining regions derived from non-human immunoglobulin that is transplanted into a human antibody framework. Humanized antibodies are typically recombinant proteins in which only the antibody complementarity-determining regions (CDRs) are of non-human origin.

Production of antibodies can be accomplished using any technique commonly known in the art. For example, the production of a polyclonal antibody can be accomplished by administering an immunogen containing the antigen of interest to an antibody-producing animal. For example, the antigen of interest (also referred to as "target antigen") can be administered to a mammal (e.g., a rat, a mouse, a rabbit, a chicken, cattle, a monkey, a pig, a horse, a sheep, a goat, a dog, a cat, a guinea pig, a hamster) or a bird (e.g., a chicken) so as to induce production of a serum containing an antigen-specific polyclonal antibody. The target antigen can be administered in combination with other components known to facilitate induction of a B-cell response, such as any appropriate adjuvant known in the art. Furthermore, the polyclonal antibody reagent can be further processed to remove or subtract any antibody members that have unacceptable affinity for antigens that are not the antigen of interest. The resulting polyclonal antibody reagent will exhibit enhanced specificity for the antigen of interest and are useful for detection and quantification purposes. Many approaches for adsorption of polyclonal antibody reagents to reduce cross-reactivity exist, are familiar to persons of ordinary skill in the art, and are encompassed by the present disclosure.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981), incorporated herein by reference in their entireties. The term "monoclonal antibody" refers to an antibody that is derived from a single clone, including any eukaryotic, prokaryotic, or phage clone, and not the method by which it is produced. Methods for producing and screening for specific antibodies using hybridoma technology are routine and well known in the art.

Antibody fragments that recognize specific target substrate sequences or structures can be generated by any technique known to those of skill in the art. For example, Fab and F(ab')₂ fragments of the invention can be produced by proteolytic cleavage of immunoglobulin molecules, using enzymes such as papain (to produce Fab fragments) or pepsin (to produce F(ab')₂ fragments). F(ab')₂ fragments contain the variable region, the light chain constant region and the CHI domain of the heavy chain. Further, the antibodies of the present invention can also be generated using various phage display methods known in the art.

As used herein, the term "aptamer" refers to oligonucleic or peptide molecules that can bind to specific target substrates of interest. Nucleic acid aptamers usually are short strands of oligonucleotides that exhibit specific binding properties to target nucleic acids (or other antigens). They are typically produced through several rounds of in vitro selection or systematic evolution by exponential enrichment protocols to select for the best binding properties, including avidity and selectivity. One type of useful nucleic acid aptamers are thioaptamers, in which some or all of the non-bridging oxygen atoms of phophodiester bonds have been replaced with sulfur atoms, which increases binding energies with proteins and slows degradation caused by nuclease enzymes. In some embodiments, nucleic acid aptamers contain modified bases that possess altered sidechains that can facilitate the aptamer/target binding.

Peptide aptamers are protein molecules that often contain a peptide loop attached at both ends to a protamersein scaffold. The loop typically has between 10 and 20 amino acids long, and the scaffold is typically any protein that is soluble and compact. One example of the protein scaffold is Thioredoxin-A, wherein the loop structure can be inserted within the reducing active site. Peptide aptamers can be generated/selected from various types of libraries, such as phage display, mRNA display, ribosome display, bacterial display and yeast display libraries.

In some embodiments, the nucleic acid-interactive protein has or can incorporate a guide nucleic acid that confers target substrate specificity. For example, Cas9, dCas-9, or other RNA/DNA guided endonucleases known in the art can be loaded with guide RNAs that confer specificity for a specific nucleic acid sequence within a target substrate. Typically, the guide RNA will have sequence complementarity with the sequence contained in the target nucleic acid substrate. The guided endonucleases can be loaded with the guide RNA(s) in a guide loading buffer at a temperature range of 4-37° C. for 1-15 min. As indicated above, the loading of the guide RNA can be performed prior to or after the coupling of the nanoparticle to the endonuclease.

The guide RNA can be constructed following published protocols. Specifically, a protospacer adjacent motif (PAM) site is identified and the flanking sequence (target sequence) is chosen to minimize off target genomic sites. The target sequence is concatenated to published guide-RNA hairpin sequences. The final guide-RNA (gRNA) can be synthesized individually by commercial oligonucleotide synthesis vendors. A pool of gRNAs can be synthesized by commercial oligonucleotide synthesis vendors to produce a pool of gRNAs in a single tube. Additionally, a DNA oligonucleotide compliment to the gRNA sequence can be synthesized with an added T7 or sp6 recognition site for an in vitro transcription reaction to produce the gRNA molecules. This can be performed for individual gRNAs or with pools of DNA complements of gRNAs. The nucleic acids can be exotic nucleic acids or contain modifications (for secondary/tertiary attachment). Non-limiting, exemplary modifications to the gRNA include the addition of one or more of biotin, biotin (azide), biotin-TEG, dual biotin, PC biotin, desthiobiotin-TEG, azide (NHS ester), acrydite, digoxigenin (NHS ester), cholesteryl-TEG, I-linker™, amino group, hexynyl, octadiynyl dU, thiol, dithiol, thiol modifier C6 S-S, PNA, locked nucleic acids, iso-G/iso-C, and the like, or any combination thereof.

Detection of Target Nucleic Acids

In some embodiments, the method further comprises imaging the targeted nanoparticle construct on the target nucleic acid substrate. Such embodiments can be performed, for example on preserved tissue samples for in situ imaging, where the targeted nanoparticle constructs provide for NP-based imaging of bound target nucleic acid substrates. For example, the presence of specific target RNA transcripts can be mapped in a particular region or the presence of a genomic element of a pathogen can be revealed among host tissue. The imaging can be the product of properties of the bi-metallic nanoparticles themselves or imaging moieties loaded thereon. Furthermore, the presences of the bound nanoparticles can be used as a quantifiable signal to infer the amount or concentration of the bound substrate, for example in color-shift assays used on a membrane or in solution for diagnostic purposes.

In some embodiments, after the targeted nanoparticle construct is assembled on the target nucleic acid substrate, unbound targeted nanoparticle constructs, or unassembled subcomponents thereof, are washed away to avoid background signal.

Enrichment of Target Nucleic Acids

In further applications, the targeted nanoparticle construct can be used to enrich, isolate, and/or purify nucleic acids molecules of interest from an initial milieu of sample components (e.g., from cellular components and/or non-target nucleic acid molecules). After enrichment, isolation, and/or purification, the target nucleic acids can be subjected to further analysis or manipulation. For example, the nucleic acids can be subjected to sequencing on any relevant platform to accomplish targeted sequencing. This can include such applications as exome sequencing, amplicon sequencing, assessing copy number variation, targeted bisulfide sequencing, large and small nucleic acid fragment sequencing on any platform (e.g., using PacBio, Illumina, nanopore technologies, and the like), mitochondrial sequencing, use of diagnostics and genotyping panels for specific genetic markers, forensics sequencing, pathogen and viral marker panels, assessing food and water quality using panel sequencing, and the like.

In applications where enrichment of the target nucleic acid is desired, unbound substrate and/or unbound components of the sample milieu are separated from the complexes of the targeted nanoparticle construct and target nucleic acid constructs.

In some embodiments, the complexes of the targeted nanoparticle construct and target nucleic acid constructs are immobilized while the unbound components of the sample are washed away. For example, in embodiments where the nanoparticles have magnetic metal components, a magnetic field can be applied to immobilize the substrate complexes during washing procedures. Removal of the magnetic field allows the complexes to go back into solution. The targeted nanoparticle construct can be separated from the target nucleic acid substrate using sample conditions (e.g., raised temperature, known denaturing buffers, and the like).

Exemplary loading buffer and wash solutions for the loading of guide RNA to the targeting moiety (e.g., Cas9) and for binding, washing, and isolating the target DNA substrate are listed in Table 1.

TABLE 1

Exemplary Loading and Wash Buffers.

| Loading Buffer | |
|---|---|
| gRNA Loading Buffer | 4-20 mM Hepes<br>10-150 mM KCl<br>0.1-1% Sucrose |
| Reaction and Wash Solutions | |
| 1 | 10-150 mM Tris-HCl<br>1-100 mM MgCl<br>0.5-5 mM ATP<br>1-50 mM DTT |
| 2 | 10 mM Bis-Tris-Propane-HCl<br>10 mM MgCl2<br>1 mM DTT<br>pH 7.0 at 25° C. |
| 3 | 10 mM Bis-Tris-Propane-HCl<br>10 mM MgCl2<br>100 µg/ml BSA<br>pH 7.0@25° C. |
| 4 | 50 mM NaCl<br>10 mM Tris-HCl<br>10 mM MgCl2<br>1 mM DTT<br>pH 7.9@25° C. |
| 5 | 50 mM NaCl<br>10 mM Tris-HCl<br>10 mM MgCl2<br>100 µg/ml BSA<br>pH 7.9@25° C. |
| 6 | 100 mM NaCl<br>50 mM Tris-HCl<br>10 mM MgCl2<br>1 mM DTT<br>pH 7.9@25° C. |
| 7 | 100 mM NaCl<br>50 mM Tris-HCl<br>10 mM MgCl2<br>100 µg/ml BSA<br>pH 7.9@25° C. |
| 8 | 50 mM Potassium Acetate<br>20 mM Tris-acetate<br>10 mM Magnesium Acetate<br>1 mM DTT<br>pH 7.9@25° C. |
| 9 | 20 mM Tris-HCl<br>25 mM Potassium Acetate<br>10 mM Magnesium Acetate<br>1 mM NAD 1<br>10 mM DTT<br>0.1% Triton ® X-100<br>pH 7.6@25° C. |
| 10 | 50 mM Tris-HCl<br>10 mM MgCl2<br>1 mM DTT<br>pH 7.5@25° C. |
| 11 | 50 mM Tris-HCl<br>10 mM MgCl2<br>1 mM ATP<br>10 mM DTT<br>pH 7.5@25° C. |
| 12 | 66 mM Tris-HCL<br>10 mM MgCl2<br>1 mM Dithiothreitol<br>1 mM ATP<br>7.5% Polyethylene glycol (PEG6000)<br>pH 7.6 @ 25° C. |
| 13 | 66 mM Tris-HCl<br>10 mM MgCl2<br>1 mM DTT<br>1 mM ATP<br>6% Polyethylene glycol (PEG 6000)<br>pH 7.6@25° C. |
| 14 | 137 mM NaCl<br>2.7 mM KCl<br>10 mM Na2HPO4<br>1.8 mM KH2PO4<br>1 mM CaCl2•2H2O<br>0.5 mM MgCl2•6H2O<br>pH 7.4 |

In other embodiments, buffer exchange and desalting columns can be used to enrich for the nanoparticle tagged nucleic acid substrates. Exemplary filters and columns include Amicon® Ultra Centrifugal Filters (Millipore) and Zeba spin columns (ThermoFisher)

It will be understood that the above embodiments, and other embodiments described herein, are provided for explanatory purposes, and are not intended to be limiting.

All publications, patents and patent applications cited herein are hereby expressly incorporated by reference for all purposes to the extent they are consistent with this disclosure.

Methods well-known to those skilled in the art can be used to construct primers and other synthetic nucleic acids, and other analytical tools such as expression vectors and recombinant bacterial cells according to this disclosure. These methods can include in vitro recombinant DNA techniques, synthetic techniques, conjugation techniques, and PCR techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

EXAMPLES

The following Examples are illustrative of specific embodiments of the disclosure and various uses thereof. They are set forth for explanatory purposes only, and are not to be taken as limiting.

Example 1

Nanoparticle Synthesis

Primary Goethite synthesis was modified from historical protocols. The 50-100 nm nanoparticle precipitate extracted for analysis, washed then acidified with 1M HCl to re-solubilize iron. Transformation to hematite followed from recrystallization of Goethite. a) R. M. Cornell and U. Schwertmann in *The Iron Oxides: Structure, Properties, Reactions, Occurrences and Uses*, (Ed: C. Reinhardt), WILEY-VCH, Weinheim, 2003, pp. 61-64; b) Berger, et al., *Journal of Chemical Education* 1999, 76, 943; c) U. Schwertmann, E. Murad, *Clays and Clay Minerals* 1983; d) R. Massart, *IEEE Trans. Magn.* 1981, 17, 1247-1248; e) P. F. Hahn, *Journal of Biological Chemistry* 1946, 163, 435-435. Stage two synthesis begins with reverse-injection of 10 ml of the acidified iron solution from stage one into the second reaction solution of dilute chloroauric acid $HAuCl_4$ 2 nm iron clusters reassemble during initiation of stage two, forming the vertices of uniform trigonal plates. The AuFe NP composite reassembly process appears to follow LaMer kinetics with corollary reference to their recrystallization. a) A. Bee, R. Massart, S. Neveu, *Journal of Magnetism and Magnetic Materials* 1995, 149, 6-9; b) V. K. La Mer, R. H. Dinegar, *J. Am. Chem. Soc.* 1950, 72, 4847-4854. The stepwise evolution of higher order structures through coordinated bridging of iron vertices by sub-nanometer gold complexes, i.e., trigonal plates into a tetragonal prism, has been visualised and is supported by theoretical and experimental simulations. a) Yuk et al., *Science* 2012, 336, 61-64; b) Norris et al., *Science* 2008, 319, 1776-1779; c) A. Packter, *Kolloid-Zeitschrift* 1960, 170, 48-52; d) J. L. Frahn, *Aust. J. Chem.* 1958, 11, 399-405; e) H. V. Tartar, J. R. Lorah, *J. Phys. Chem.* 1924, 29, 792-798; d) M. Neidle, *J. Am. Chem. Soc.* 1917, 39, 2334-2350; f) A. Benrath, *J. Praia. Chem.* 1917, 96, 190-201.

Example 2

Nanoparticle Synthesis Using the Devices of the Present Disclosure

All glassware was meticulously cleaned [i.e., HF acid cleaning and rinsed with milliQ water triple-distilled in glass. Liquids were degassed and sealed under Argon prior to assembly. Solids were dried and degassed and stored under high vacuum and all solutions prepared with water triple distilled in glass and exhaustively degassed prior to use. High-vacuum single-manifold Schlenk line was fitted with metal-to-glass seals and gated manometers; a motorized glass stirring rod was installed. Shaft speed was monitored at a constant 300 RPM by a non-contact RheinTacho digital tachometer. The temperatures of solutions were measured continuously with non-contact IR and glass thermometers immersed in silicon oil baths surrounding the reaction chamber. An Alcatel 2063 rotary-vane and Drytel 31 turbomolecular vacuum pump were coupled via a triple-set switching valve to the LPSP Schlenk line fitted with primary and secondary $LN_2$ gas traps. The full synthetic line was evacuated via flexible stainless steel hoses (1.5 in. i.d.) to $10^{-4}$ Pascal (Pa) and fluted with argon grade 6 thrice prior to each synthesis. Helium back-pressure loaded injection introduced liquids into a reaction chamber evacuated to <$10^{-4}$ Pa, backfilled and maintained at 1-2 Pa.

Example 3

Characterization of Low Pressure Solution Phase Single Schlenk Line Synthesized Isotope-Doped Mixed-Metal NANoparticles [LPSPSSL-MMNPS].

Radioisotopes were incorporated into MMNP nanoparticles to act as radiotracers in the signal generating moiety of prototype nanoscale composites for use as in diagnostic and therapeutic applications. High-resolution electron microscopy, electron paramagnetic resonance (EPR), electron energy loss (EELS), and X-ray dispersive spectroscopy (XRDS) were used to determine composition, purity and structure of "cold" mixed-metal nanoparticles. Comprehensive analysis of individual LPSPSSL-MMNP preparations revealed highly uniform size, structure and composition of individual nanoparticle reaction products.

Figure 3A:
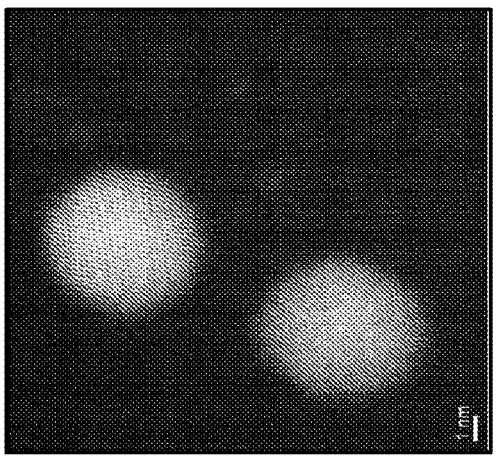
FIG. 3A is a high-resolution electron micrograph of a nanoparticle including a 5 nm gold$^{198}$ (Beta particle emitter) radioisotope core surrounded by stable gold$^{197}$ shell; in accordance with an embodiment of the disclosure.
Figure 3D:
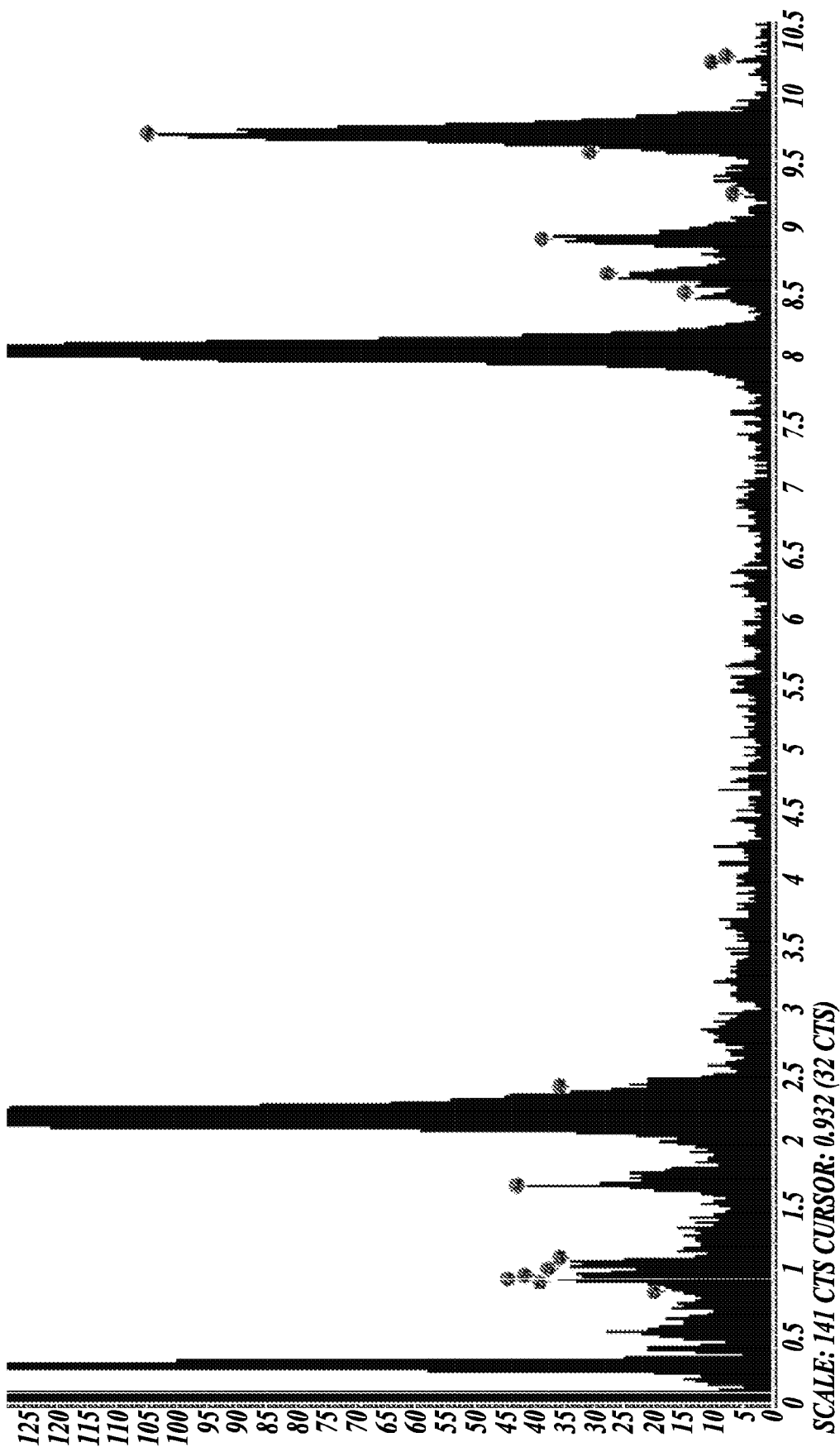
FIG. 3D shows x-ray diffraction spectroscopy spectra of the nanoparticles of FIG. 3A.
Figure 4:
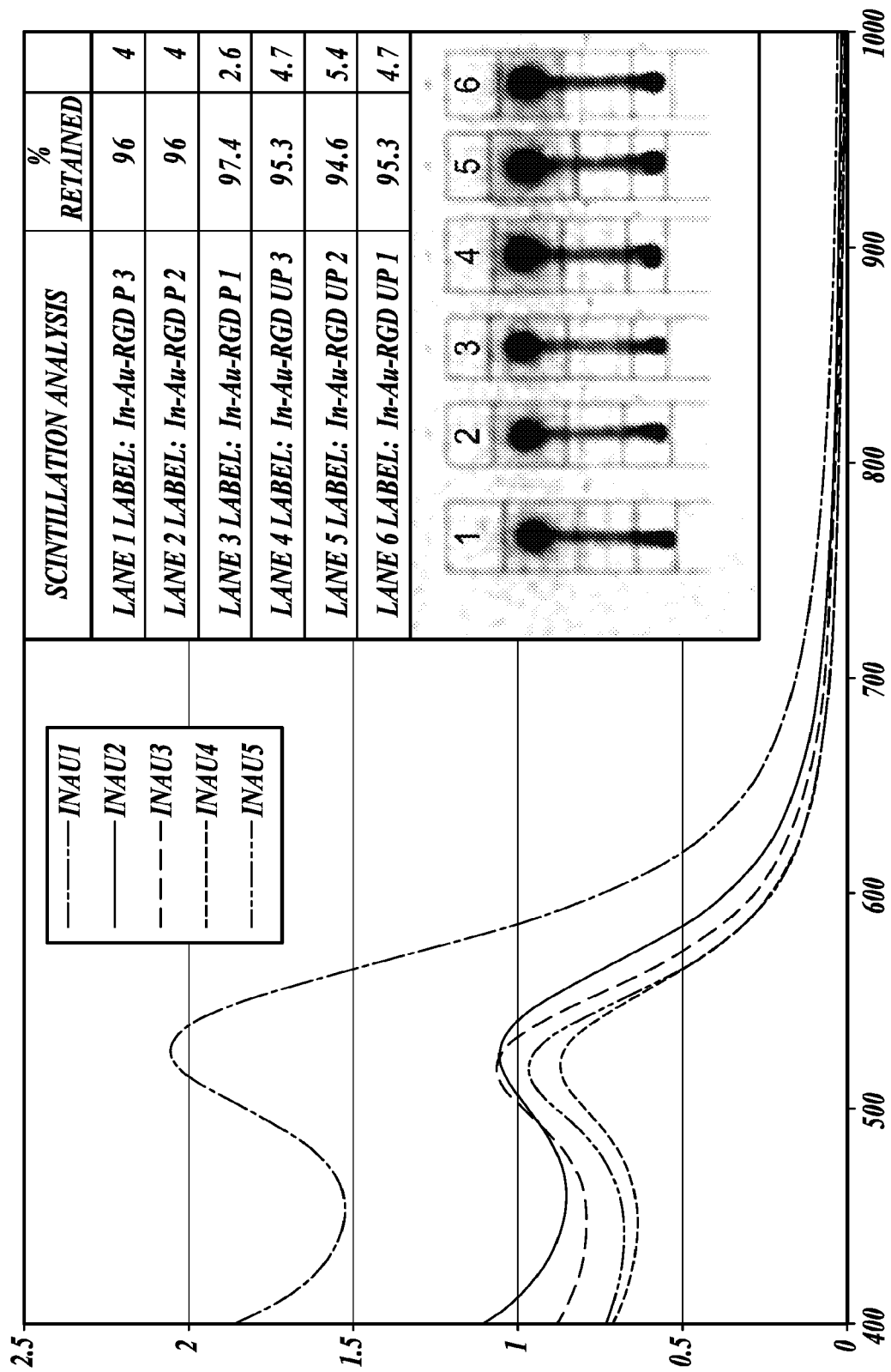
FIG. 4 graphically illustrates absorbance spectra of nanoparticles of FIG. 3B, thin layer chromatography of the nanoparticles (inset bottom), and scintillation data of the nanoparticles (inset top)

As shown in FIGS. 3A and 3D, respectively, ultra-high-resolution transmission electron microscopy (UHR-TEM) and XRDS spectra reveal atomic lattice structure in pure solutions of uniform gold-coated $^{198}Au$ (gold isotope 198) core-shell nanoparticles. These were synthesized via deposition of "cold" gold $^{197}Au$ atoms onto the surface "hot" $^{198}Au$ isotope seed-cores in solution. Activity and purity were further analyzed by scintillation and spectroscopy.

Figure 9A:
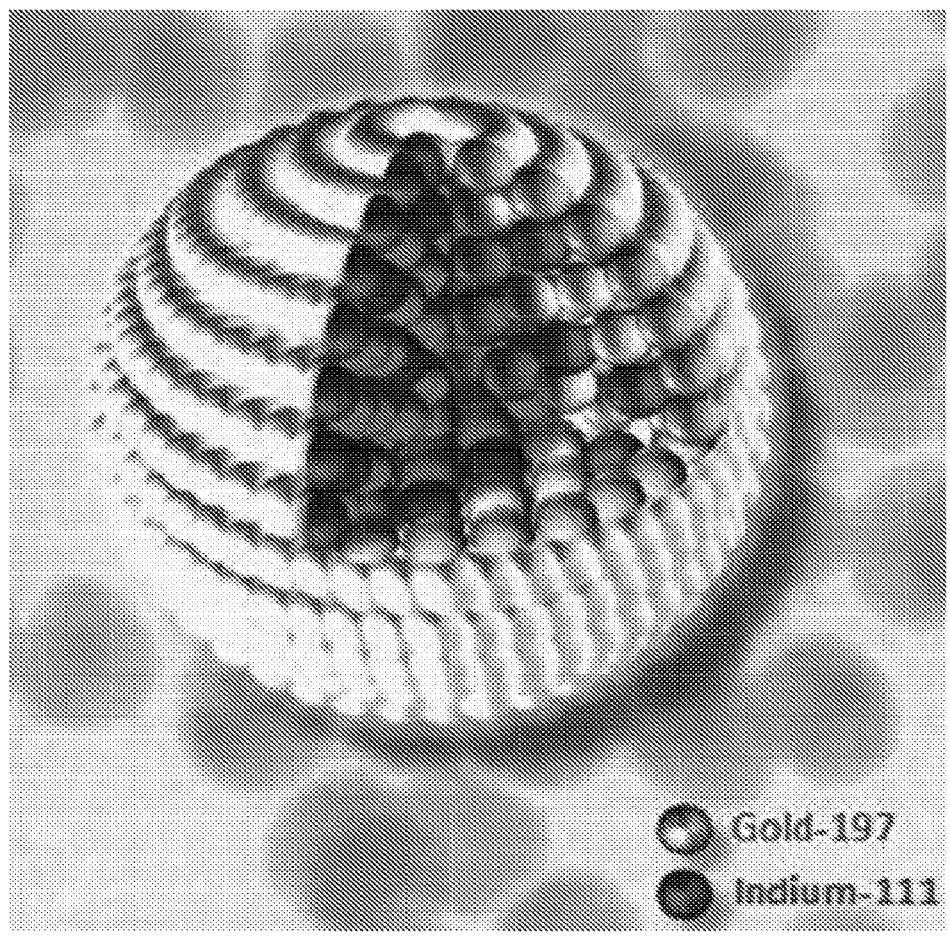
FIG. 9A is an illustration of a gold indium nanoparticle, in accordance with an embodiment of the disclosure.
Figure 9B:
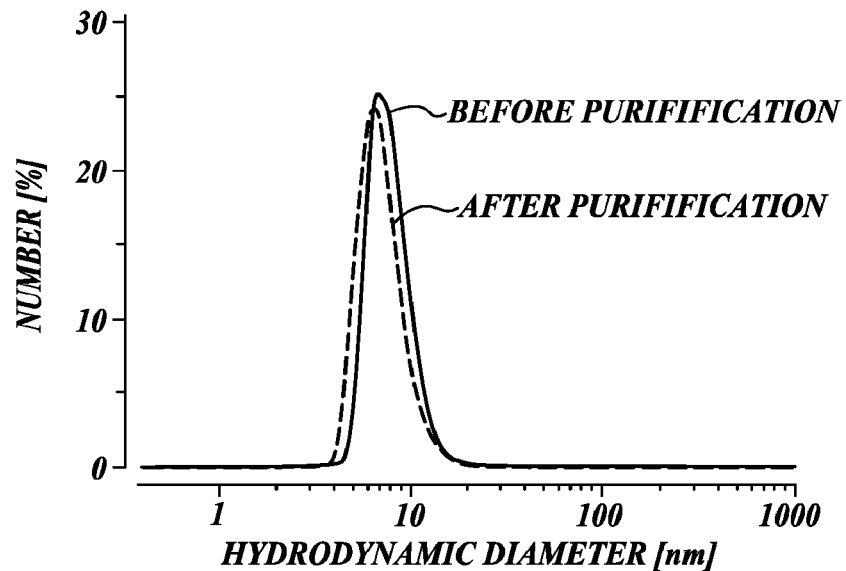
FIG. 9B graphically illustrates hydrodynamic diameter of nanoparticles as illustrated in FIG. 9A, in accordance with an embodiment of the disclosure, before and after purification.
Figure 9C:
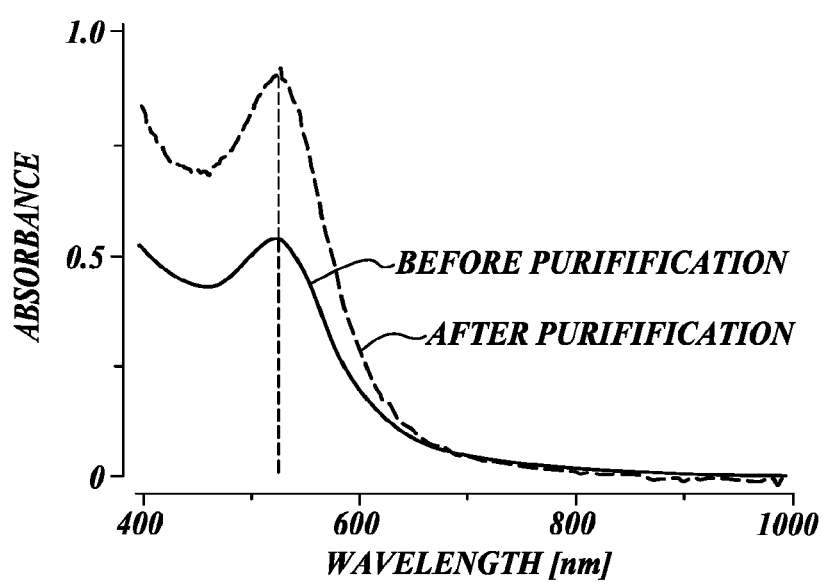
FIG. 9C graphically illustrates UV-visible absorbance spectroscopy of nanoparticles as illustrated in FIG. 9A, in accordance with an embodiment of the disclosure.
Figure 9D:
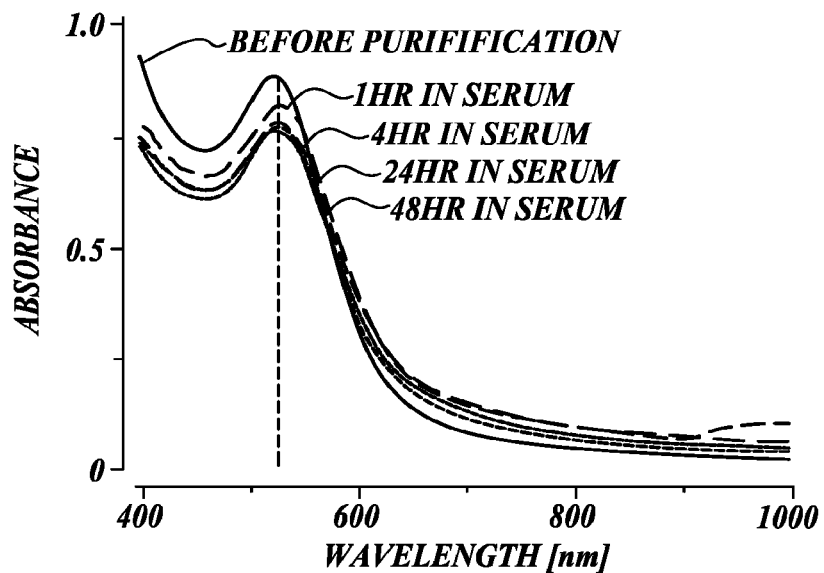
FIG. 9D graphically illustrates UV-visible absorbance spectroscopy of conjugated targeted nanoparticles, in accordance with embodiments of the disclosure, in serum.
Figure 9E:
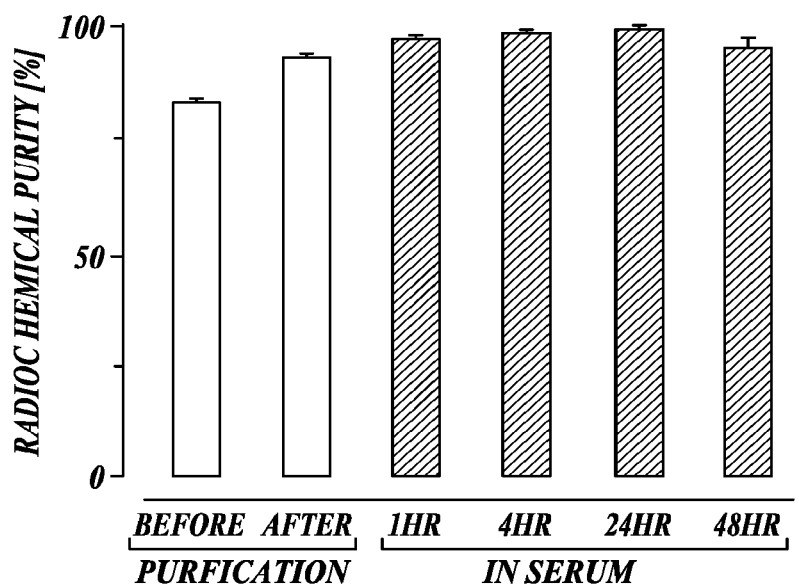
FIG. 9E graphically illustrates scintillation analysis of conjugated targeted nanoparticles, in accordance with an embodiment of the disclosure, pre- and post-purification and in human blood serum.

Rapid LPSPSSL synthetic protocol incorporating Indium ($^{111}In$) into a gold nanoparticle complex (See model in FIG. 9A) by co-reductive precipitation was used. Intercalation of $^{111}indium$ into a gold nanoparticle is accomplished by a co-reductive deposition of both metals. See generally FIGS. 9A-9E. This methodology facilitates use in nuclear medicine diagnostic and therapeutic applications. FIG. 3B shows UHR-TEM of [$^{197}Au@^{111}In$] nanoparticles having uniform 7 nm radioisotope indium core/gold shell nanoscale composites. Activity and purity were further analyzed by scintillation and spectroscopy (FIG. 4).

Hydrodynamic size measurements showed narrowly distributed indium-111 labeled gold particles of 7-8 nm before and after purification. UV-visible absorbance spectra of the indium-111 labeled gold particles before and after purification showed a stable maximum at 524 nm. See FIG. 9C. UV-Visible spectroscopy pre- and post-purification of Au@$^{111}$In MMNPs in spin-down centrifugation columns shows consistent wavelength readings. This supports constant sizing and composition over time and process; i.e., negligible or no-visible separation of targeted conjugates and no change in sizing. High serum stability of the indium-111 labeled gold particles was found in the presence of human blood serum at up to 48 hours. See FIG. 9E.

UV-visible absorbance spectroscopy of conjugated targeted of the distributed indium-111 labeled gold nanoparticles in serum reveals long-term stability. See FIG. 9D. Consistent readings reflect a gradual disappearance of MMNPs in vivo.

Gold-coated gadolinium, Au@$^{68}$Gd, nanoparticles were synthesized via LPSPSSL protocol. Ultra-pure solutions of 5 nm particles were examined by UHR-TEM (See FIG. 3C), and further studied by XRDS, scintillation and elemental analysis.

Spectroscopy characterization of the Au@$^{111}$In MMNP nanoparticles closely matches their TEM images and size distribution measurements. See FIG. 4. The absorbance spectra exhibit a stable maximum at 524 nm indicating the absence of aggregation.

Purity was measured via analysis of thin-layer chromatography (Radio-TLC). See FIG. 4, inset bottom. Radio-TLC was carried out by spotting 1 microliter of each sample (lanes 1-6); developed TLC strips were then placed in an autoradiography cassette with a multi-sensitive storage phosphor screen and scanned using a phosphor imager (Perkin Elmer). Scans were quantified using the OptiQuant Acquisition and Analysis commercial software. Scans of lane 1-6 (FIG. 4, inset bottom) reveal homogenous purities of individual "raw" sols >94%. See FIG. 4, inset top. Physical evidence in all studies is used to triangulate and verify high purity and stability of raw MMNP sols and targeted conjugates. The same study techniques are applied to QC (quality control) of all LPSPSSL-MMNPs.

Example 4

Activity and Integrity of Affinity-Targeted Au@$^{111}$In MMNP Conjugates In Vivo An Indium-111 labeled gold nanoparticle platform, modified with the tumor targeting sequence arginine-glycine-aspartate (RGD), was developed and utilized for tumor cell targeting in-vitro and in-vivo studies. See generally FIGS. 10A-10E. Dynamic light scattering (DLS) Zeta-sizing analysis showed that targeting RGD ligands conjugated to the particle surface resulted in a 3-4 nm increase of the hydrodynamic diameter. See FIG. 10C. UV-visible spectroscopy of the RGD-modified indium-111 labeled gold particles in the presence of human blood serum revealed a stable surface plasmon resonance peak at up to 48 hours, indicating the absence of aggregation. See FIG. 10D.

Figure 10B:
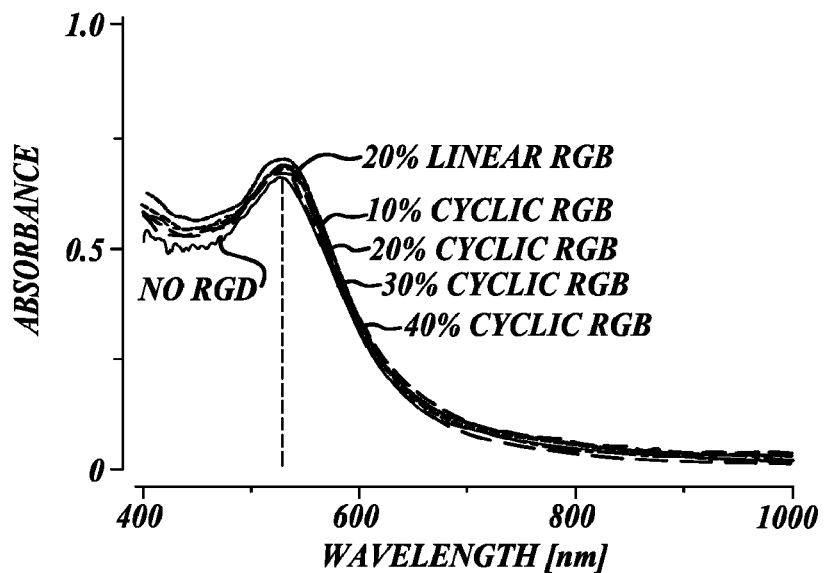
FIG. 10B graphically illustrates UV-visible absorbance spectra of nanoparticles, as illustrated in of FIG. 10A, having varying concentrations of surface ligands on the surface of nanoparticles.
Figure 10C:
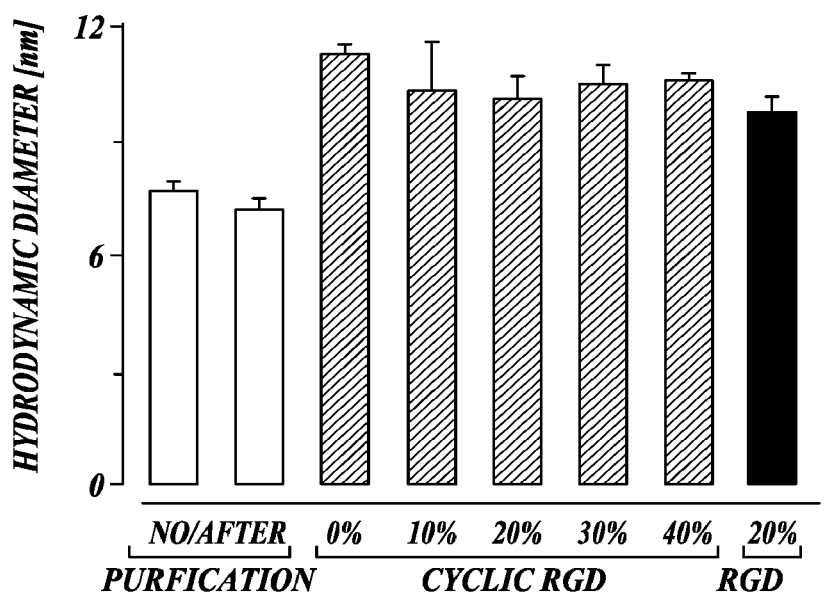
FIG. 10C graphically illustrates hydrodynamic diameter targeted and purified nanoparticles, in accordance with embodiments of the disclosure.
Figure 10D:
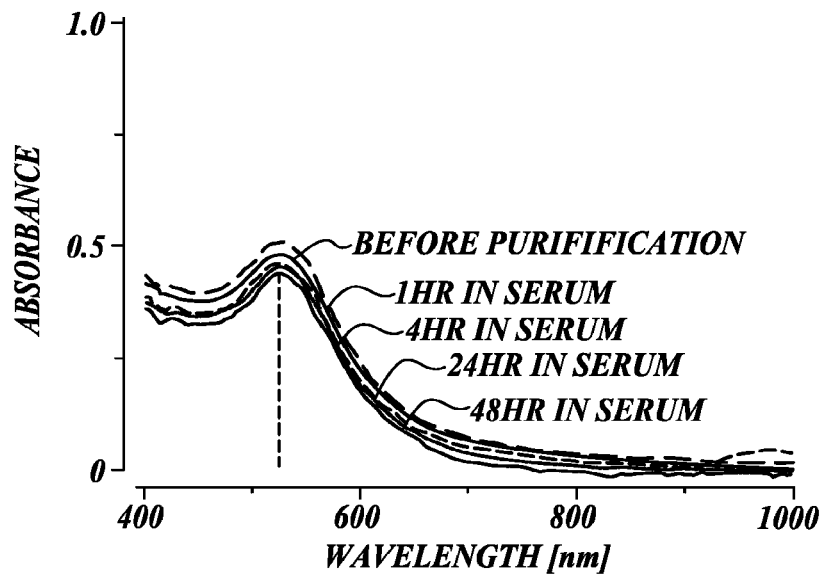
FIG. 10D graphically illustrates UV-visible absorbance spectroscopy of nanoparticles before purification and in human serum after various periods of time, in accordance with embodiments of the present disclosure.
Figure 10E:
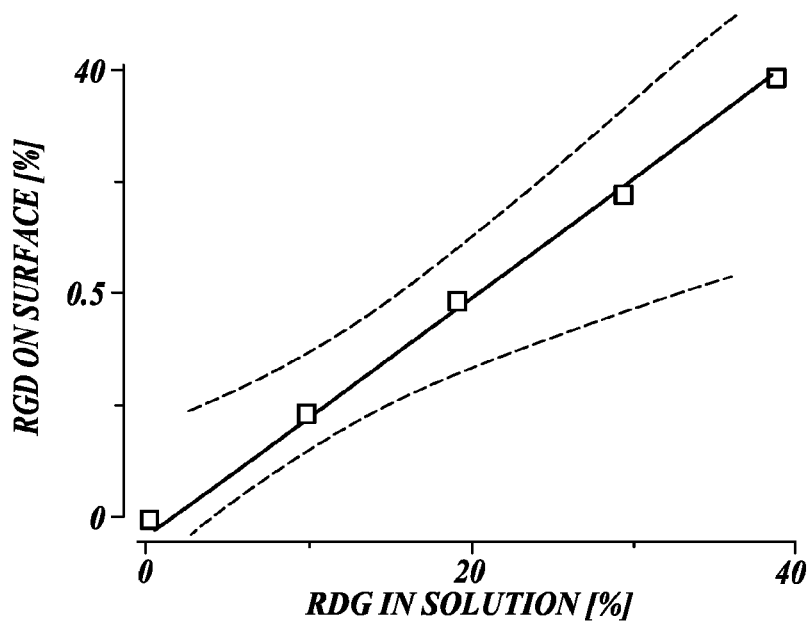
FIG. 10E graphically illustrates a decrease in RGD in solution during surface conjugation of ligand to nanoparticles with a concomitant increase of RGD ligands on MMNP surfaces, in accordance with embodiments of the present disclosure.

FIG. 10A is a schema of cyclic and linear RGD-ligands attached to the surface model of Au@111In MMNPs. Background image is a high-resolution electron micrograph of aforementioned complexes. FIG. 10B compares UV-visible spectral analysis of nanoparticles having varying concentrations of surface ligands. FIG. 10C shows Zeta-sizing of unpurified and purified "naked" particles compared to MMNPs conjugated various concentrations of Cyclic and Linear RGD ligands. FIG. 10E graphically illustrates an analysis of a decrease of RGD in solution during surface conjugation of ligand to nanoparticles with a concomitant increase of RGD ligands on MMNP surfaces.

Example 5

EDAC DOTA-Tate, DOTA-Toc Conjugation to Fluorophores and Radioisotope NPS

Figure 6A:
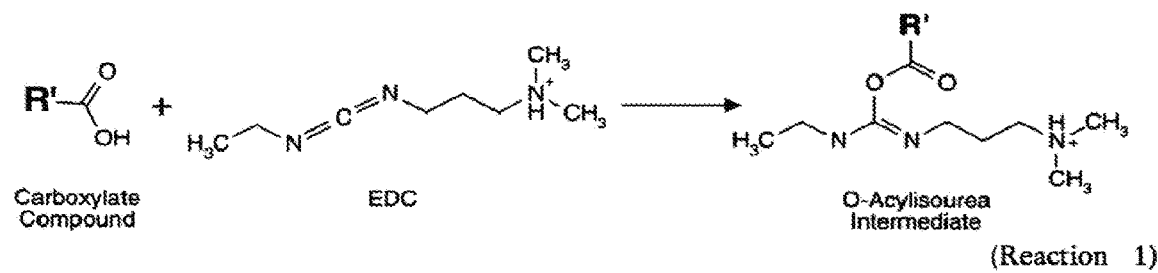
FIG. 6A includes schema of EDAC-mediated binding reactions of carboxylated compounds (—R') with amines (—R$_{1,2}$) present on both affinity R' ligand (DOTA-TOC) and R₂ NHS-derivatized fluorophore AF-350; in accordance with an embodiment of the disclosure.
Figure 6A:
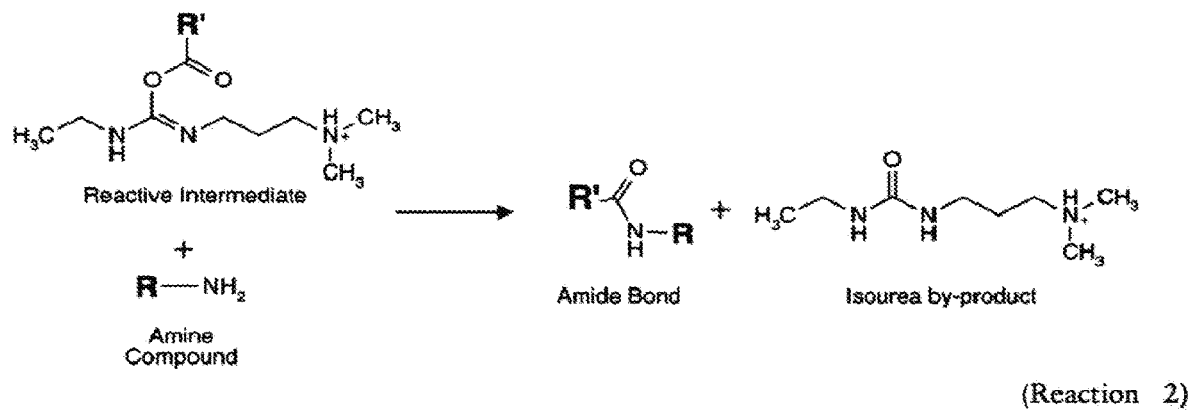
Figure 6A:
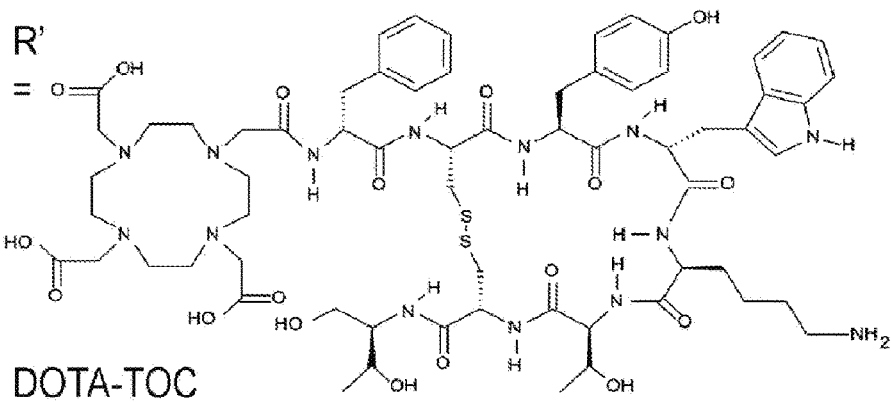
Figure 6A:
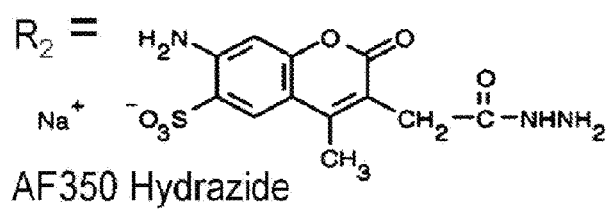
Figure 6B:
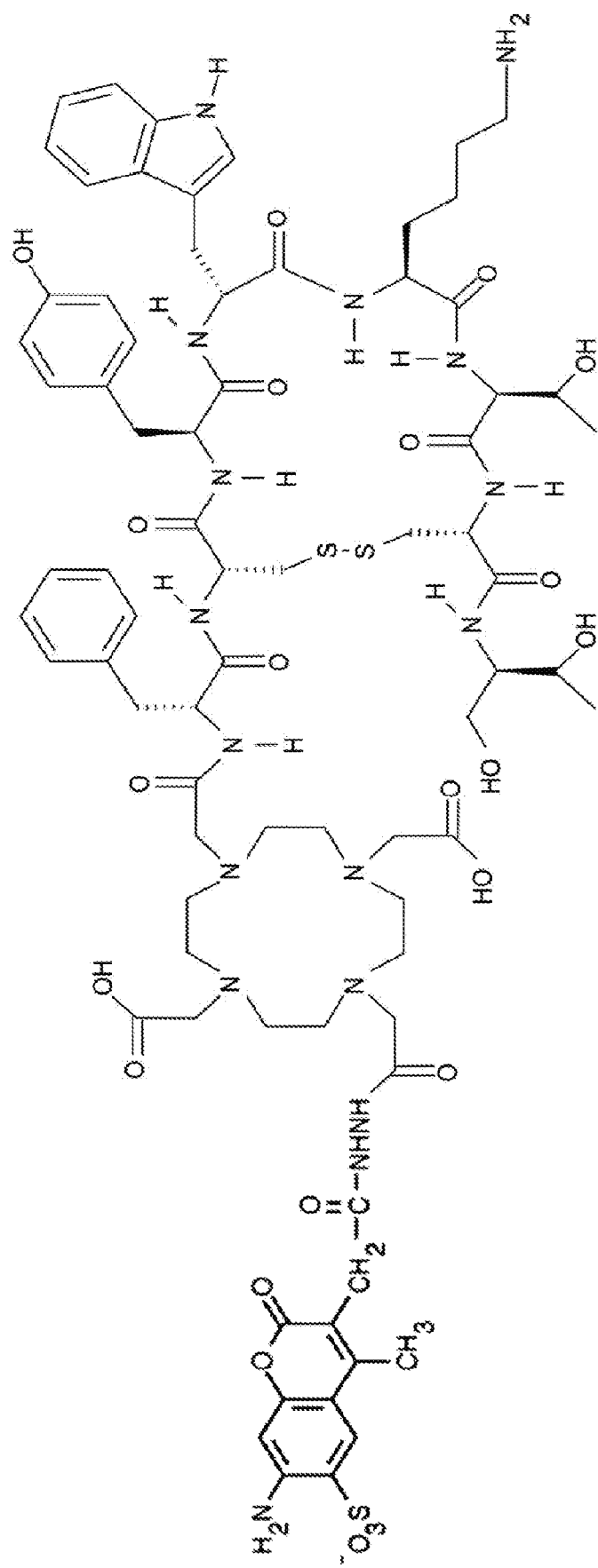
FIG. 6B provides structure of fluorophore-affinity targeted complex prior to conjugation to individual MMNPs, in accordance with an embodiment of the disclosure.
Figure 7A:
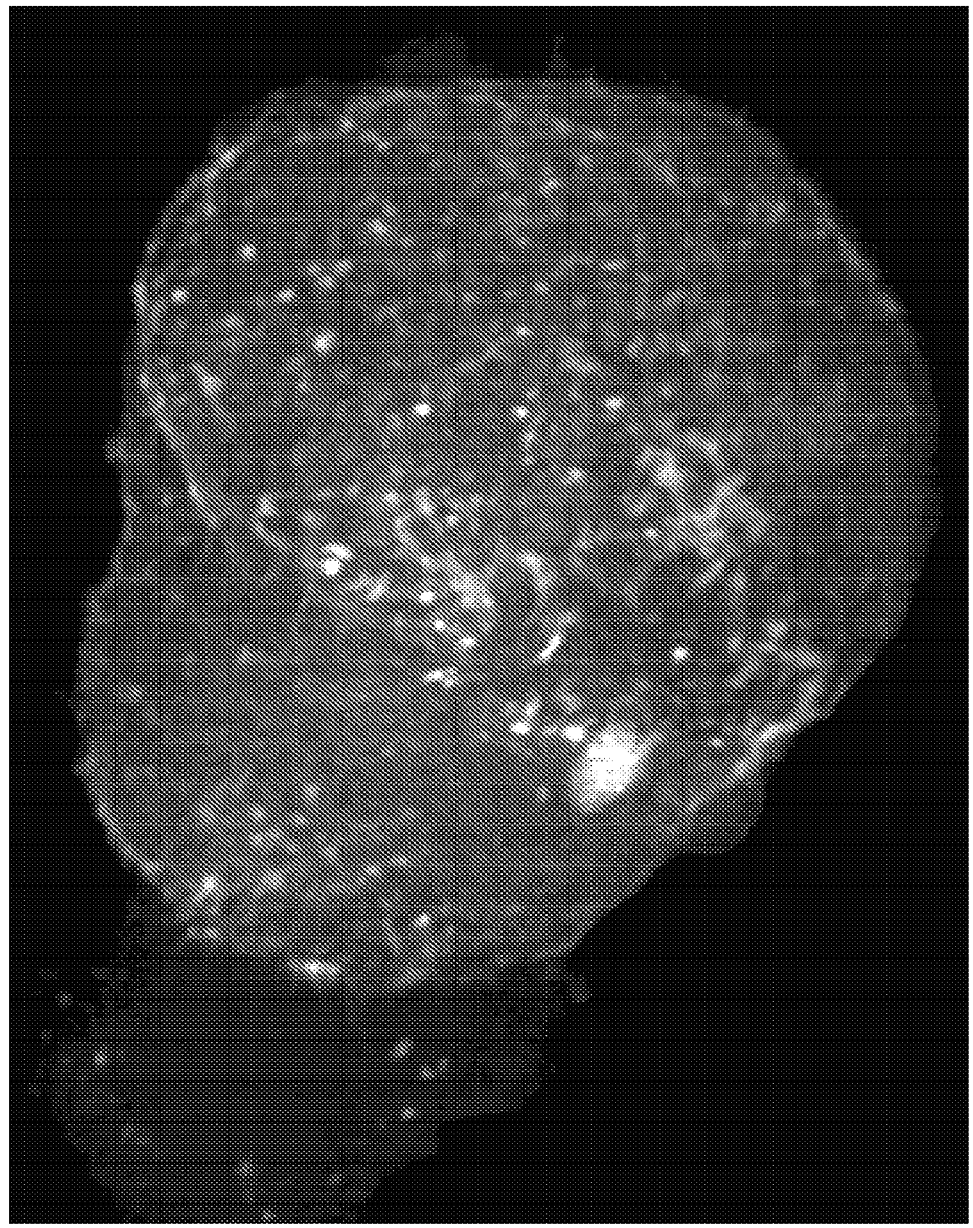
FIGS. 7A-7D are correlative confocal scanning light microscopy images showing effective penetration of tumor-targeted fluorescent, radioisotope nanoparticles, in accordance with an embodiment of the disclosure.
Figure 7B:
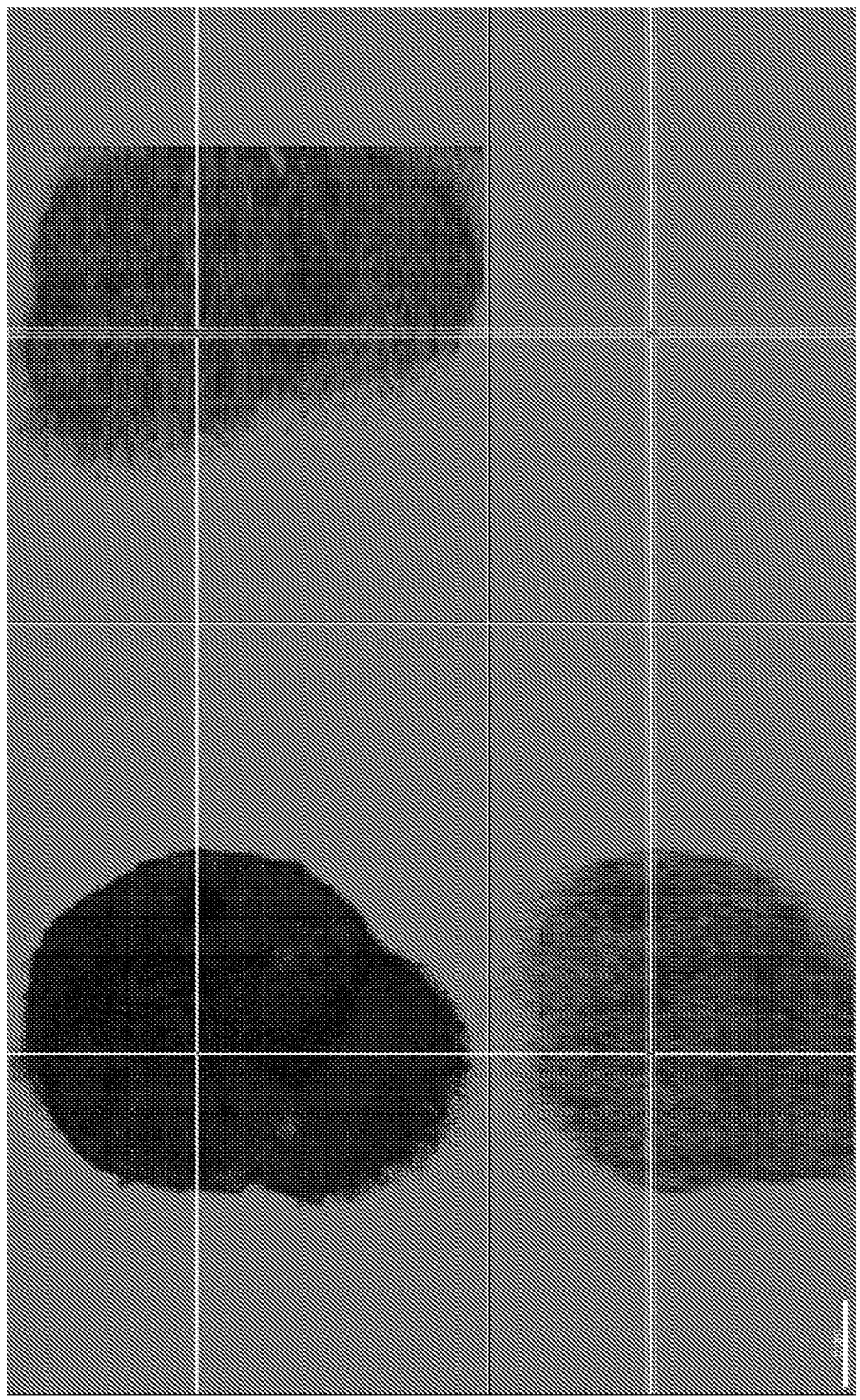
Figure 7C:
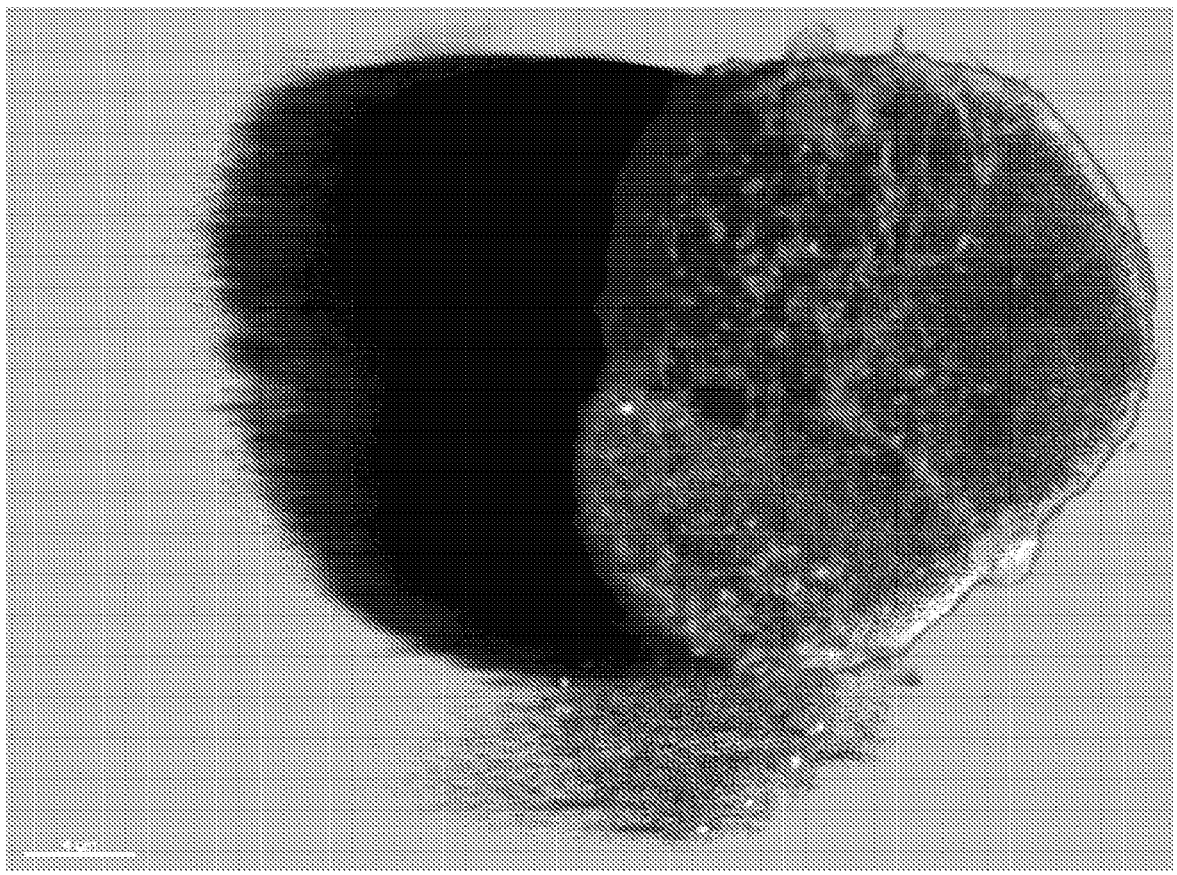
Figure 7D:
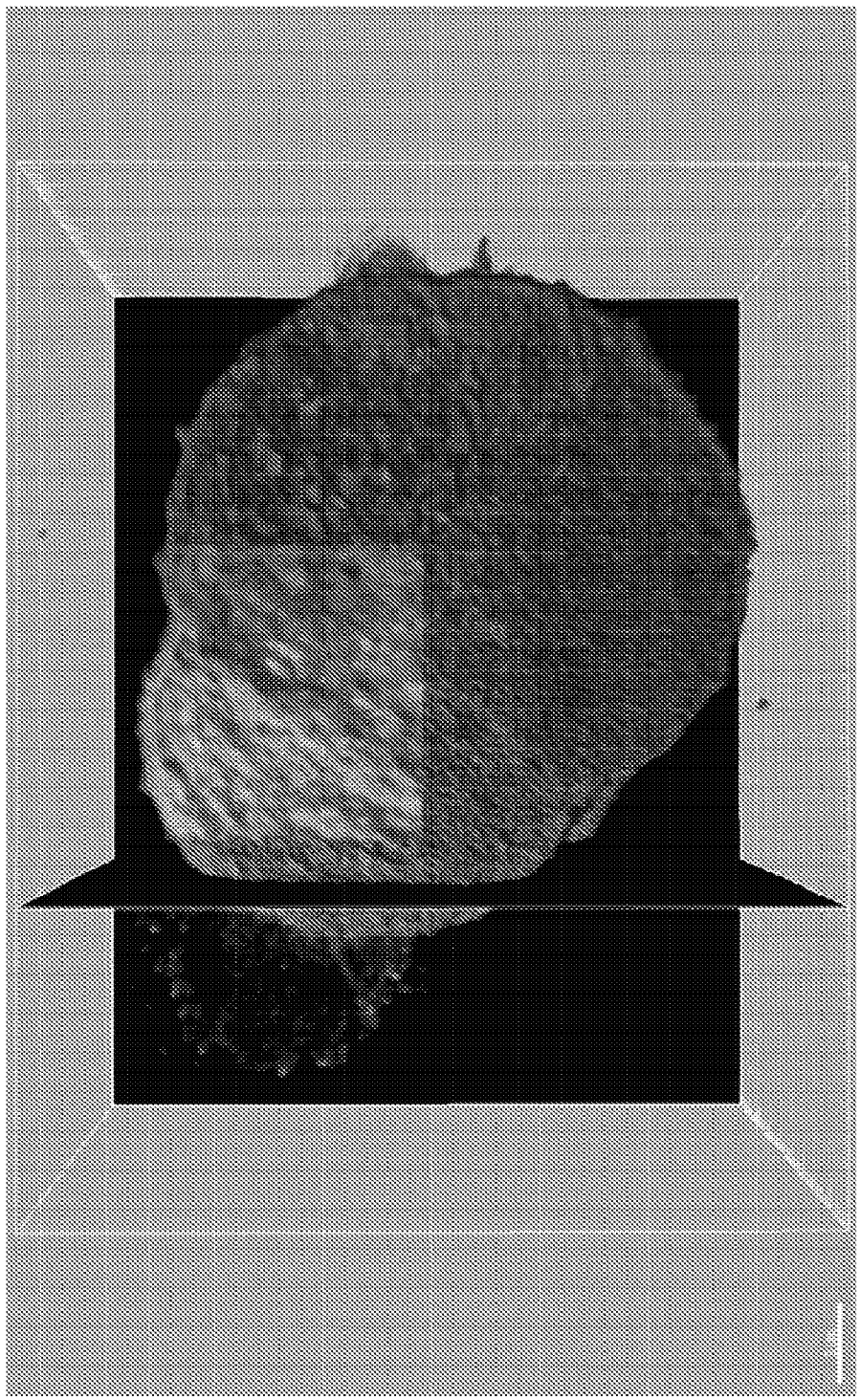
Figure 8A:
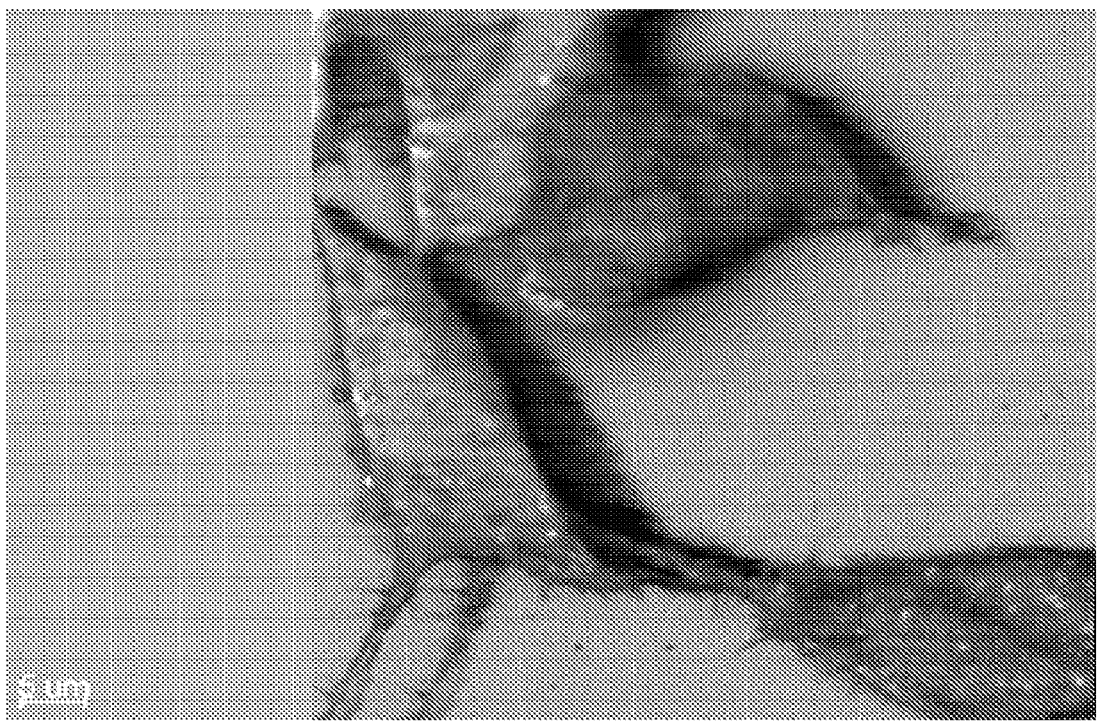
FIGS. 8A-8E are images showing volumetric imaging of AF-350/DOTA-TOC conjugates in ATT 20 cells, in accordance with an embodiment of the disclosure.
Figure 8B:
Figure 8C:
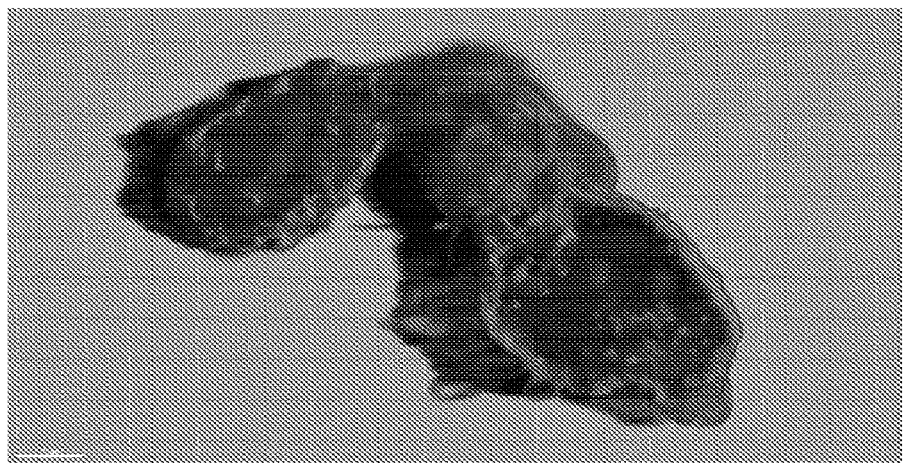
Figure 8D:
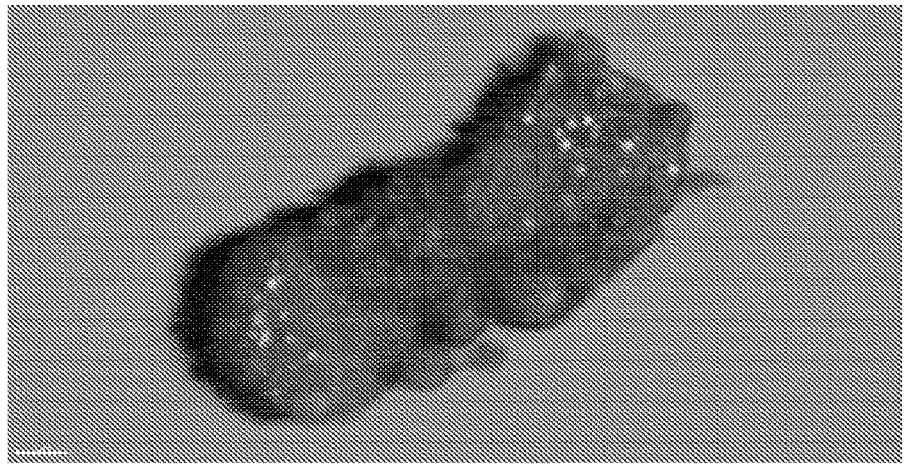
Figure 8E:
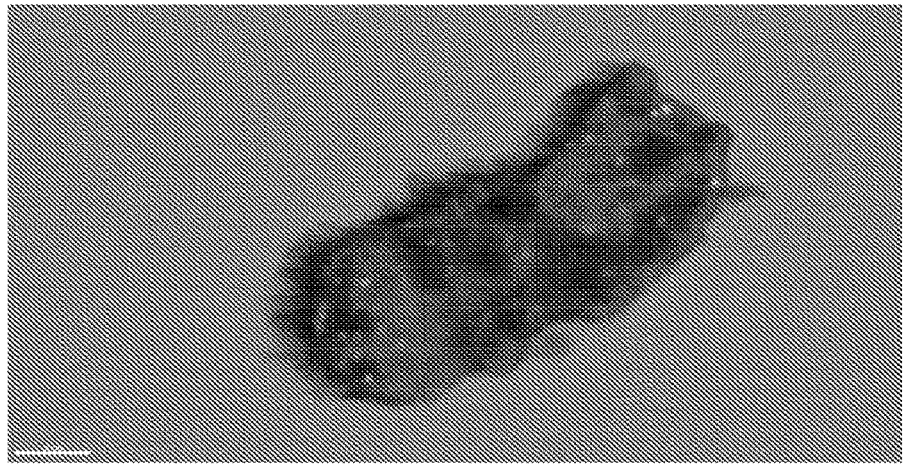

A modification of a two-step protocol (Grabarek and Gergely, 1990) for the activation of proteins with EDC/sulfo-NHS and subsequent conjugation with amine-containing compounds is illustrated in FIGS. 6A and 6B. The variation in the pH of activation from that described above provides greater stability for the active ester intermediate. At pH 6.0, the amines on the protein will be protonated and therefore be less reactive toward the sulfo-NHS esters that form. In addition, the hydrolysis rate of the esters is dramatically slower at slightly acid pH. Thus, the active species may be isolated in a reasonable time frame without significant loss in conjugation potential. To quench the unreacted EDC, 2-mercaptoethanol is added to form a stable complex with the remaining carbodiimide, according to Carraway and Triplett (1970). In the following protocol, sulfo-NHS is used instead of NHS so that active ester is more water-soluble and ester hydrolysis is slowed (Anjaneyulu and Staros, 1987; Thelen and Deuticke, 1988).

DOTA-TATE and DOTA-TOC have 4 carboxyl groups, 3 of which are free to bind COOH-reactive fluorophores, e.g. hydrazines et al. AF350-hydrazide was chosen out of a wide array of COOH-reactive fluorophores due to low MW and putative heightened membrane permeability. EDC or EDAC, 1-ethyl-3-(3-dimethylaminopropyl)carbodiimide is used to facilitate and enhance this reaction.

Prepare:
a) 0.1M MES Buffer For 1 L: Dilute 19.5 Free MES acid into 500 ml millipure $H_2O$ under stirring. Bring final volume to 1 L and bring to pH6 with NaOH
b) Dilute 2 mg DOTA-TATE (or DOTA-TOC) into 1000 μl 0.1M MES Buffer. In other words, 2 mg/ml in a 1.5 ml Eppendorf
c) Fluorophore Preparation:
Make stock solution 55 mM of AF350 (or other AF-Hydrazine fluorophore) i.e., Place 1 mg AF350 Hydrazide MW 349.29 into 260 μl DMSO
d) Immediately prior to conjugation place 10 mg EDAC in 1 ml MES Buffer
DOTA-TATE Fluorophore Conjugation:
1. Add 25 μl (c) Stock AF 350 sol'n. to (b) (1 ml DOTA-TATE/MES pH6)
2. Add 15 μl (d) Stock EDAC to above mix of AF 350 and DOTA-TATE/MES in Eppendorf Cap Eppendorf and invert to mix at least 4×. Incubate 2-3 h RT.

A reaction schematic is illustrated in FIGS. 6A and 6B. Cells contacted with the nanoparticles of EXAMPLE 3 are depicted in FIGS. 7A-7D.

Example 6

Figure 5A:
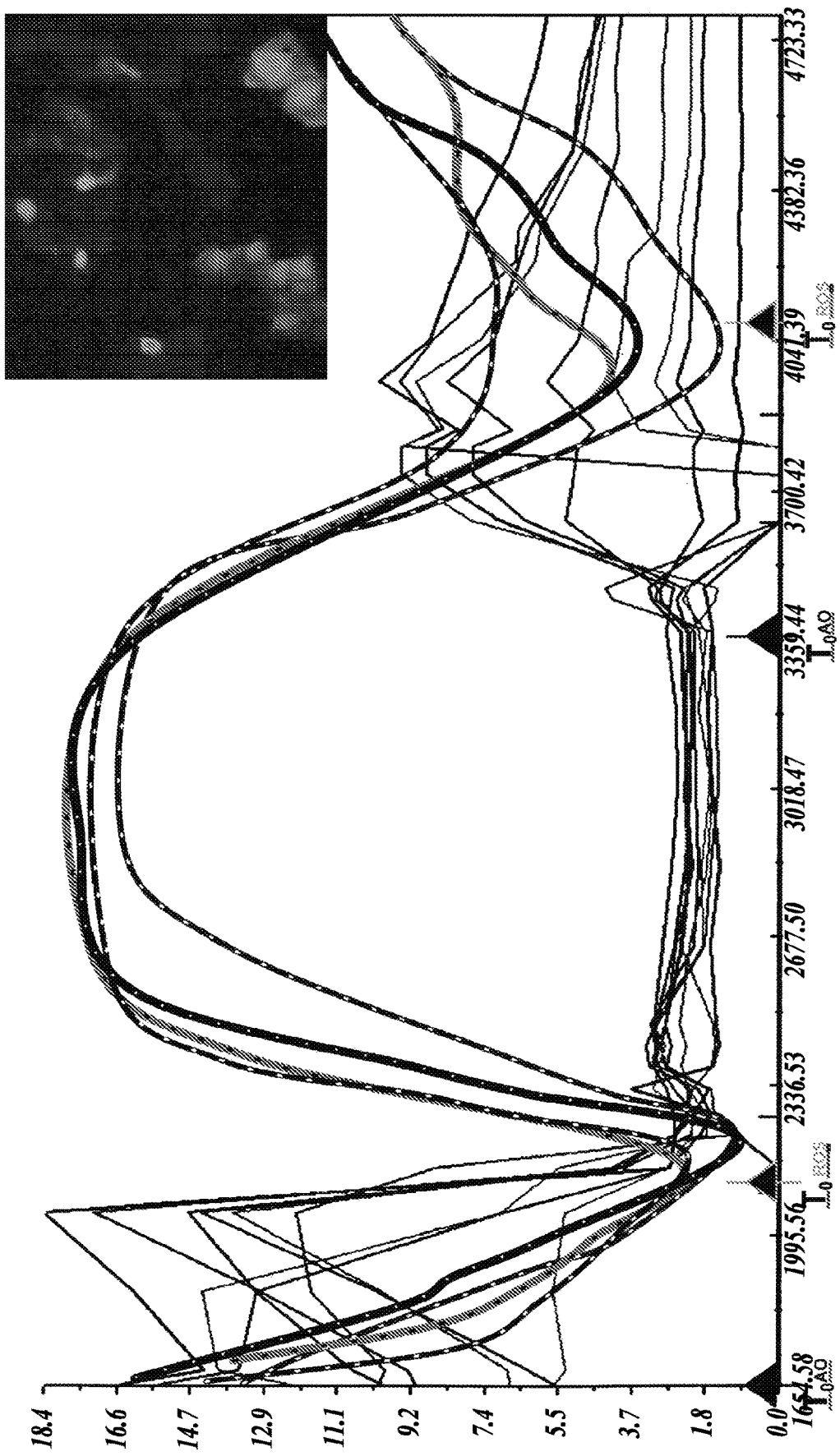
FIG. 5A graphically illustrates ratiometric imaging of anti-oxidant Ro-GFP cells with surface-derivatized nanoparticles including antioxidant compounds, in accordance with an embodiment of the disclosure.
Figure 5B:
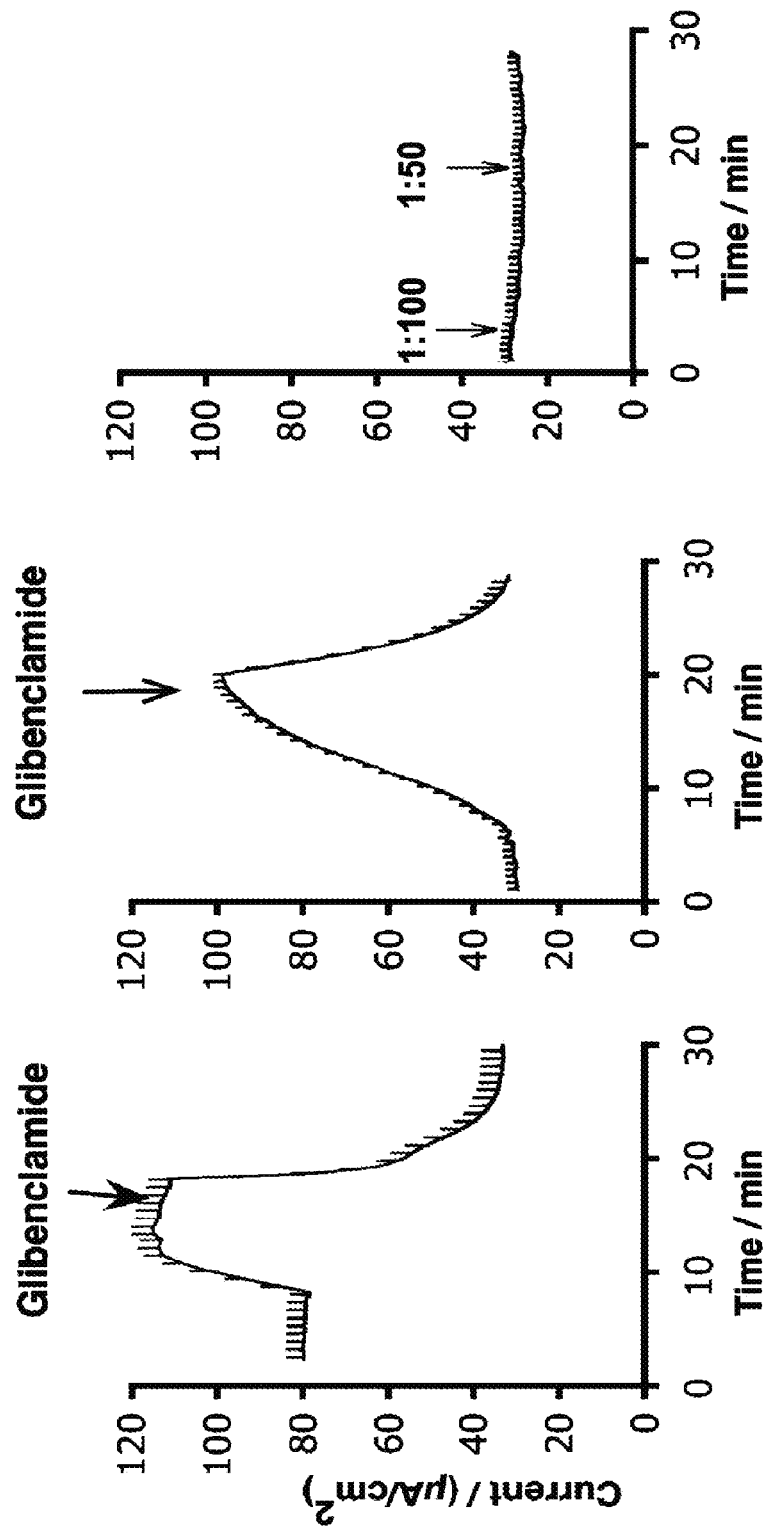
FIGS. 5B and 5C graphically illustrate Ussing Chamber measurement of effect of DHLA/GSH delivery to primary tissue culture from ΔCFTR− (cystic fibrosis primary tissue)
Figure 5C:
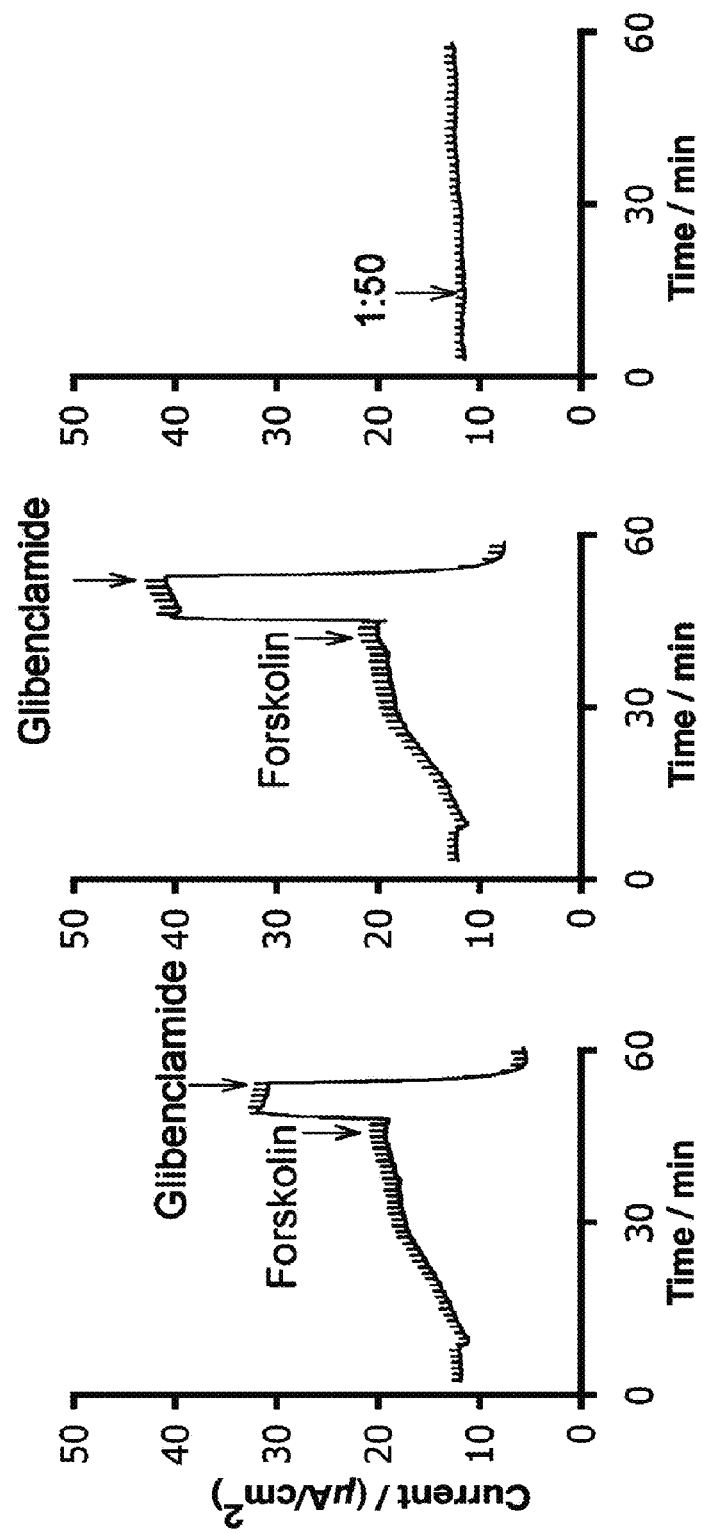

Functional Toxicity Assays of Naked Nanoparticles and Nanoparticles Surface Derivatized with Antioxidant Compounds Two different toxicological assays are presented:
A. Ratiometric imaging of anti-oxidant Ro⁻ GFP cells (FIG. 5A)
B. Ussing Chamber measurement of effect of DHLA/GSH delivery to primary tissue culture from ΔCFTR– [cystic fibrosis primary tissue] (FIGS. 5B and 5C)

In assay A, cells were transformed incorporating a redox-(reduction/oxidation) sensitive probe, RoGFP. These cells were then exposed to a strong oxidant (peroxide). This is presented in FIG. 5A. The addition of peroxide is noted time $T_0ROS$ on the x-axis (seconds). Nanoparticles (Au@Au NP) synthesized with surface physiological antioxidants (AO): DHLA and reduced GSH (glutathione) envelopes were added at $T_0{}^{AO}$ and the antioxidant activity measured via ratiometric imaging on y-axis, of live cells, FIG. 5A insert. Four separate experiments were conducted with n≥100 cells for each trial (thick dotted lines). Individual controls for each antioxidant trial are traced in thin solid lines. A dramatic reduction in the oxidative activity immediately followed addition of AO Nanoparticles. This is a prototypic assay for NO– and free radical toxicity responses in live cells (1-4).

In assay B, primary (human) tissue culture was placed in multiwell Ussing Chambers (2×4) with a constant flow of physiological buffer. The Ussing experimental apparatus enables real-time measurement of micro conductivity (charge), hence viability and function, of ion-channels across thousands of cells in ex vivo tissue over extended periods (days). Think of this as massive patch-clamp technology. The putative effect of antioxidants (AO) in cystic fibrosis therapy has been demonstrated (5). Lung tissue from CF patients ΔCFTR– are defective in Cl (chloride) ion channel transport. Antioxidants open the defective channel temporarily. We wanted to see if by stabilizing the AO on the surface of nanoparticles we could amplify and extend the effect. Results in FIG. 5B (1:50 diluiton of AO NP) and FIG. 5C, (1:100 dilution of AO NP) show this to be the case. Forskolin and Glibenclamide were used to establish the maximal and minimal (cell death) possible limits. Addition of AO NP at $T_0$ shows a marked increase in ion channel function in ΔCFTR– tissue (normally defective). Naked nanoparticles were used as controls in the last frames of FIGS. 5B and 5C.

Conclusions: The results of this Example indicate that nanoparticles surface stabilized with biological antioxidants provide a vector for therapies on a nontoxic nanoparticle platform.

1. Hanson et al. Investigating mitochondrial redox potential with redox-sensitive green fluorescent protein indicators. *J Biol Chem* (2004) vol. 279 pp. 13044-13053
2. Dooley et al. Imaging dynamic redox changes in mammalian cells with green fluorescent protein indicators. *J Biol Chem* (2004) vol. 279 pp. 22284-22293
3. Austin et al. Oxidizing potential of endosomes and lysosomes limits intracellular cleavage of disulfidebased antibody-drug conjugates. *P Natl Acad Sci USA* (2005) vol. 102 (50) pp. 17987-17992

4. Lohman and Remington. Development of a family of redox-sensitive green fluorescent protein indicators for use in relatively oxidizing subcellular environments. *Biochemistry-Us* (2008) vol. 47 (33) pp. 8678-8688

5. Schwarzer et al. Organelle redox of CF and CFTR-corrected airway epithelia. *Free Radical Bio Med* (2007) vol. 43 (2) pp. 300-316

Example 7

Quantitative Volumization of Micro-Metastatic Islets in a Mouse Cancer Model

Presently, there is a void in the detection in the micro-metastatic spread of many cancers. This is a lack of crucial information and influences the management decision of all metastatic cancers. Fluorescently tagged immuno-affinity probes targeted to a subtype of Somatostatin receptors on the surface of tumor cells (ATt20) were used to specifically detect putative cancer in micro-metastatic islets from a tumor in situ. Visualization and quantification of correlative confocal microscopy was used to determine specificity and sensitivity of probes.

Six-week old nude athymic mice were subcutaneously injected in the femoral region with cancer cells. In-vivo studies were performed when the xenografts had reached approximately 5 mm$^3$. At this point, 1 MBq of purified tumor-targeted indium-111 labeled gold nanoparticle conjugates were injected via the tail vein. After 4 hours, mice were sacrificed and organs and tumors were removed and weighed. Untargeted indium-111 labeled gold nanoparticles served as negative controls. Imaging studies on micro-metastacies were performed 4 hours after injection.

A maximum intensity projection (MIP) is generated by standard "top-down" fluorescent imaging of a micro-metastatic islet (tumor). A MIP image provides an overview of internal and external volumes but only in two dimensions and each is projected on the other, and lacks spatial information.

Optical sections can be generated in X, Y and Z axis by confocal scanning laser microscopy (CSLM). Correlative mapping of each axis permits accurate localization and quantification of targeted fluorescent probes in situ.

With the application of modern microscopy software, a virtual light source can be generated to cast a shadow through all 3 axes producing a volumized "3D shadow projection." See FIGS. 7A-7D.

Advanced software enables reconstruction of optical sections into a dynamic 3D model in real-time. This model can be sectioned at will, "sliced" (black planes) through any axis and its internal composition analyzed at the nanometer scale from point to point. We used commercial software, Imaris, from Bitplane, to produce these images.

Example 8

Targeted Mmnp Nanoparticle Uptake

Targeted MMNP nanoparticle uptake was studied in cell lines expressing various integrin levels. The high-integrin expressing human melanoma cell line, M21, was used along with low-integrin expressing M21-L cells, as a control cell line. In addition, an integrin-expressing human glioblastoma cell line, U87-MG, was used, and specific binding was tested with blocking experiments as controls.

Fluorescently tagged (AF-350) DOTA-TOC affinity conjugates were attached to 6 nm MMNP nanoparticles. These complexes were purified and incubated with ATt20 host cells for 4 hours (37° C., 5% $CO_2$). See FIGS. 8A-8E.

Cells over-expressing Somatostatin sub-type were cultured directly on coated multi-well slides. Controls do not exhibit any penetration of nanoparticle complexes targeted to Somatostatins. Experimental samples exhibit blue "puff ball" clusters known to form from internalized surface receptors.

Example 9

MMNP-Labelled Enzymes Targeted to DNA Map Function to Structure

This Example describes examples of enzymes labelled with MMNPs of the present disclosure.

The rolling circle model of DNA replication in bacterial plasmids has been proposed for a long time. FIG. 17A is an ultra-high resolution scanning-electron micrograph revealing an MMNP-labelled EcoR1 restriction enzyme attached to a pBR 322 *E. coli* plasmid undergoing rolling circle replication (thread circle).

FIG. 17B is an electron microscopy image of a cryo-biology sample prepared and modified application of special high-resolution imaging techniques, establishing the highest limits of near-native structural resolution within the DNA double helix. A DNA model is inserted over the EM image for purposes of illustration.

Gold and iron nanoparticles were synthesized and bound to restriction enzymes and affinity ligands (here, monoclonal IgGs) to map sub-molecular domains on DNA and proteins in situ. See FIG. 17C.

5 nm gold NPs were bound to restriction enzymes BamH1 (FIG. 17E) and EcoR1 (FIG. 17F) to map sequence-specific restriction sites on bacterial plasmids and mtDNA in situ in micrographs of FIGS. 20E and F respectively.

Example 10

Tracking and Mapping Cancers Via Molecular Domains

Tenascin (TNCN) is a six-armed macromolecule implicated in breast cancer. Sub-molecular Fibronectin type 3 domains (FNIII) were mapped on TNCN molecules with gold NP-labelled monoclonal antibodies (IgGs). IgGs binding the seventh FNIII domain on TNCN were produced and conjugated to 1 nm gold nanoparticles and incubated with TNCN. They were cryo-fixed and examined by ultra-high resolution in-lens scanning electron microscopy (modified Hitatchi 55000 UHR-SEM) with a YAG crystal back-scattered electron (BSE detection) that permitted mapping ultrastructural sub-domains within a sub-nanometer radius. See FIG. 18, left.

A three-dimensional model of the monoclonal IgG bound to the TNCN molecule was reconstructed through multiple defocus micrograph sections. See FIG. 18 (right). Data for the molecular models of both IgG and FNIII domains were obtained via multiple Protein Data Base sources (PDB online), reconstructed with the Swiss PDB viewer and inserted into the model.

As shown in FIG. 18, with the nanoparticles of the present disclosure, we are able to visually map function and structure on the nanoscale via our MMNP probes, i.e., the sub-molecular domains on the extracellular matrix protein, TNCN, via functional binding of an IgG to specific sites corresponding to the neural cell adhesion molecule Contactin F11. Function and structural mapping is verified through UHR-SEM BSE detection of 1 nm gold nanoparticles bound to IgGs.

Example 11

Binding and Isolation of Target Nucleic Acids with Nanoparticle Composites of the Present Disclosure This example describes an illustrative embodiment of the disclosed targeted nanoparticles applied to selectively bind and isolate a target nucleic acid molecule for further analysis.

Cas-9 (or dCas-9) protein is conjugated to a multi-metal nanoparticle (NP; as described above) in a reaction solution in the presence of a reducing agent. The conjugation reaction can be in a range of 1 min to 24 hours and at temperatures ranging from 4-37° C. The reaction is terminated by standard purification methods. Once purified, the conjugate complex can be used for targeting the substrate of interest after guide-RNA loading (gRNA) if using Cas-9, dCas-9. Alternative RNA- or DNA-guided endonuclease, or TALENS can also be employed in place of the Cas-9 or dCas-9.

The targeted NP complex is combined with the target substrate in a reaction buffer at a temperature range of 4-37° C. for 1-30 min. If the nanoparticle has an iron core, then the substrate:NP:dCAS-9 complex is immobilized with a magnet and the supernatant removed. The remaining substrate:NP:dCas-9 complex is re-suspended in a wash buffer, then immobilized and supernatant removed. This wash is optionally repeated, for example, three times. The final DNA can be removed from the dCas-9 (or other protein) by heat denaturation at 90-98° C. for 2-5 min or under pH 8-14. The resulting DNA product can be used as a substrate for PCR, qPCR, additional molecular modifications (blunt repair, A-tailing, ligation, etc.), next generation sequencing, microarray hybridization, and the like.

Example 12

Binding and Isolation of Target Nucleic Acids with a Multi-Metal Nanoparticle Composites of the Present Disclosure The following example describes an illustrative embodiment of the disclosed targeted nanoparticles applied to selectively bind and isolate a target nucleic acid molecule for further analysis. In this embodiment, the nucleic acid-interacting protein (e.g., Cas-9 or dCas-9 protein) that specifically targets the nucleic acid is assembled with the multi-metal nanoparticle after it has selectively bound to the substrate nucleic acid of interest.

First, dCas-9 is loaded with gRNA's in a reaction buffer at a temperature range of 4-37° C. for 1-15 min. After gRNA loading, the substrate DNA/RNA (1 pg-10 µg) is added and dCas-9 locates the compliment of the loaded gRNA. This reaction occurs in a reaction buffer at a temperature range of 4-37° C. for 1-30 min. Once the reaction is completed, nanoparticles are added to the reaction followed by an addition of a reducing agent. The conjugation reaction can be as short as 1 min or as long as 24 hours and at temperatures ranging from 4-37 C. The reaction is terminated by standard purification methods or by nanoparticle immobilization if the nanoparticle has an iron core. If the particle has an iron core, then the substrate:NP:dCAS-9 complex is immobilized with a magnet and the supernatant removed. The remaining target substrate:NP:dCas-9 complex is re-suspended in a wash buffer, then immobilized and supernatant removed. This wash is repeated about three times. The final DNA can be removed from the dCas-9 (or other protein) by heat denaturation at 90-98° C. for 2-5 min or under pH 8-14. The resulting DNA product can be used as a substrate for PCR, qPCR, additional molecular modifications (blunt repair, A-tailing, ligation, etc.), next generation sequencing, microarray hybridization, and the like.

Example 13

Figure 14:
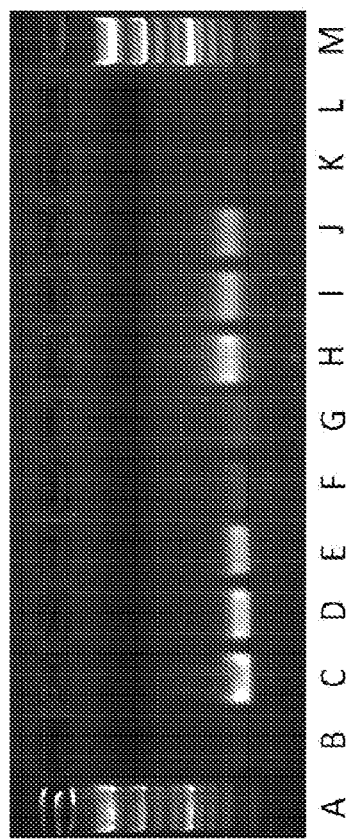
FIG. 14 includes images of electrophoresis gels showing enrichment for targets and not for the non-target, after removing the non-target by washing from the reaction, in accordance with an embodiment of the disclosure.
Figure 14:
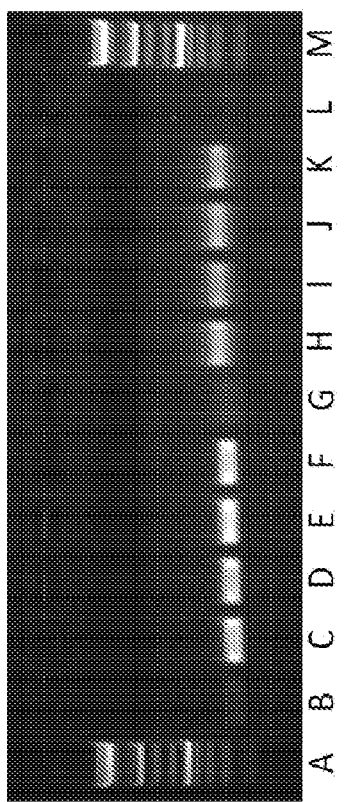

Enrichment of Several Nucleic Acid Targets with Nanoparticles According to the Present Disclosure In an illustrative assay three different DNA species were assayed in a single tube for targeted enrichment using the above approaches. Target DNA target 1 (4.5 kb), DNA target 2 (120 bp), and non-target DNA (120 bp) was added to the same tube. The two target DNAs were enriched using different targeted nanoparticle constructs incorporating (d)Cas-9 with guide RNAs that hybridize to different sequences within each of DNA target 1 and DNA target 2, respectively. The initial supernatant was collected when immobilizing the constructs with a magnetic field. This initial supernatant, as well as the supernatants collected during several rounds of washing, were used as template for PCR detection of the DNA constructs. The results are illustrated in FIG. 14. The lanes on the left and right gels are listed below in TABLE 2.

TABLE 2

| Lane | Left Gel | Right Gel |
| --- | --- | --- |
| A | O' generuler 1 kb Plus Ladder | O'generuler 1 kb Plus Ladder |
| B | Target 1 PCR Product of Supernatant From DNA Capture Reaction | Target 1 PCR Product of Supernatant From DNA Capture Reaction |
| C | Target 1 PCR Product of Wash #1 Supernatent Post DNA Capture | Target 1 PCR Product of Wash #1 Supernatent Post DNA Capture |
| D | Target 1 PCR Product of Wash #2 Supernatent Post DNA Capture | Target 1 PCR Product of Wash #2 Supernatent Post DNA Capture |
| E | Target 1 PCR Product of Wash #3 Supernatent Post DNA Capture | Target 1 PCR Product of Wash #3 Supernatent Post DNA Capture |
| F | Target 1 PCR Product of NP:dCas-9 Captured DNA After Three Washes | Target 1 PCR Product of NP:dCas-9 Captured DNA After Three Washes |
| G | Target 2 PCR Product of Supernatant From DNA Capture Reaction | Non-Target PCR Product of Supernatant From DNA Capture Reaction |
| H | Target 2 PCR Product of Wash #1 Supernatent Post DNA Capture | Non-Target PCR Product of Wash #1 Supernatent Post DNA Capture |
| I | Target 2 PCR Product of Wash #2 Supernatent Post DNA Capture | Non-Target PCR Product of Wash #2 Supernatent Post DNA Capture |
| J | Target 2 PCR Product of Wash #3 Supernatent Post DNA Capture | Non-Target PCR Product of Wash #3 Supernatent Post DNA Capture |
| K | Target 2 PCR Product of NP:dCas-9 Captured DNA After Three Washes | Non-Target PCR Product of NP:dCas-9 Captured DNA After Three Washes |
| L | Negative control PCR | Negative control PCR |
| M | O'generuler 1 kb Plus Ladder | O'generuler 1 kb Plus Ladder |

Figure 15:
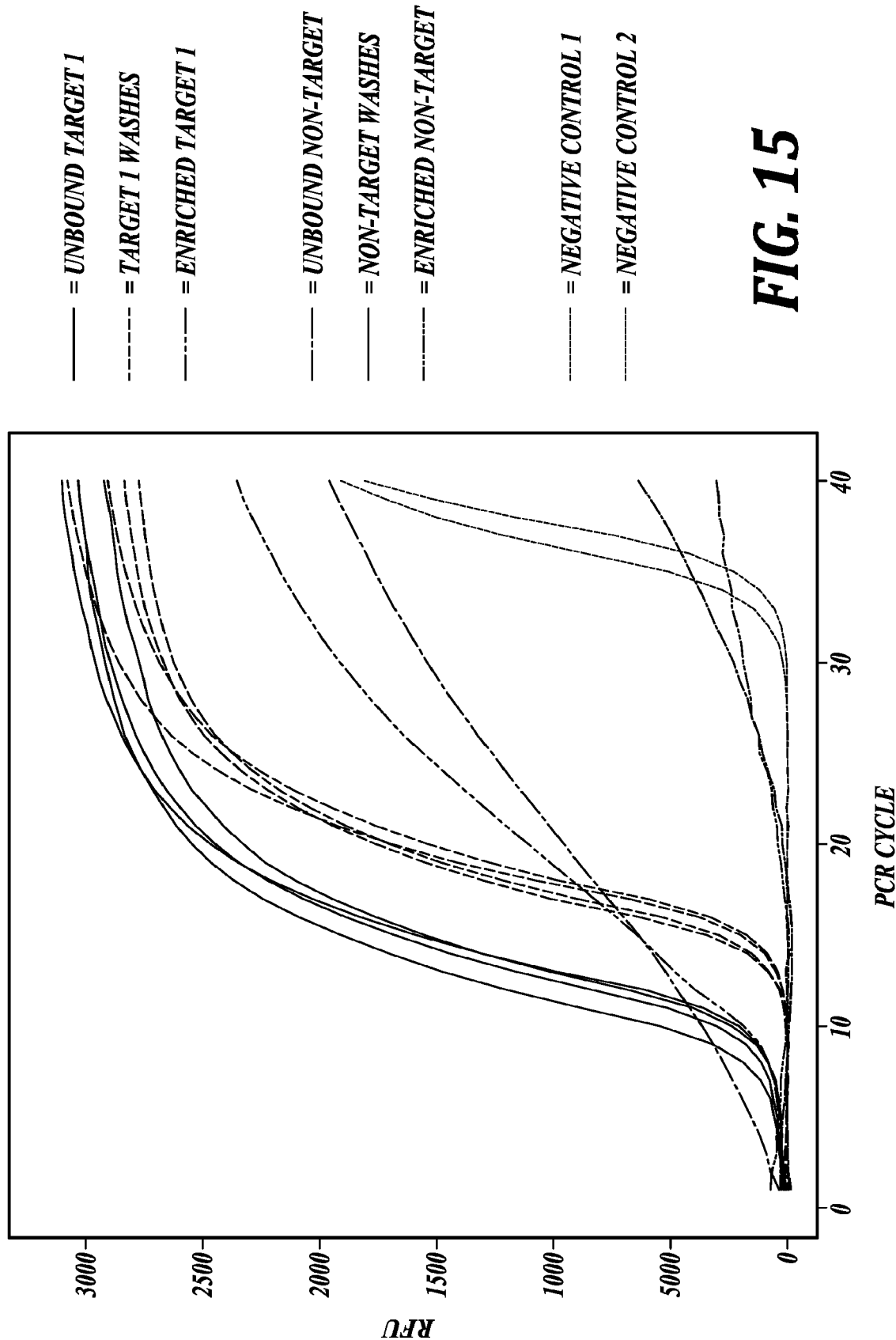
FIG. 15 graphically illustrates results of qPCR of DNA of a target, a non-target of FIG. 15A, and their respective unbound pools, showing less amplification occurred for the "Unbound Target 1" than for "Unbound Non-Target", indicating enrichment specificity, in accordance with an embodiment of the disclosure.

Quantitative PCR was performed on the DNA enriched for Target 1 DNA, Non-Target DNA, or their respective unbound pools and washing rounds. Two negative controls were performed that lacked input DNA. As illustrated in FIG. 15, less amplification occurred for the "Unbound Target 1" than for "Unbound Non-Target", suggesting enrichment specificity. This is further supported by the faster rate of exponential amplification of the Non-Target Washes than the Target 1 washes. More dramatically, the amplification of the final enrichment for Target 1 vs. Non-Target is dramatic. Little amplification occurs for the "enriched Non-Target" relative to the "enriched Target 1", relative to negative controls. This highly suggests enrichment for the target using this novel approach.

As used herein, the singular forms "a", "an", and "the" include plural referents unless the context clearly dictates otherwise. For example, reference to a "nucleic acid" means one or more nucleic acids. It is generally noted that the use of the term "or" in the claims is used to mean "and/or" unless explicitly indicated to refer to alternatives only or the alternatives are mutually exclusive, although the disclosure supports a definition that refers to only alternatives and "and/or."

Unless the context clearly requires otherwise, throughout the description and the claims, the words "comprise," "comprising," and the like are to be construed in an inclusive sense as opposed to an exclusive or exhaustive sense, such as in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue. Words such as "about" and "approximately" imply minor variation around the stated value, usually within a standard margin of error, such as within 10% or in some cases 5% of the stated value.

Disclosed are materials, compositions, and components that can be used for, in conjunction with, and in preparation for the disclosed methods and compositions. It is understood that when combinations, subsets, interactions, groups, etc., of these materials are disclosed each of various individual and collective combinations is specifically contemplated, even though specific reference to each and every single combination and permutation of these compounds may not be explicitly disclosed. This concept applies to all aspects of this disclosure including, but not limited to, steps in the described methods and components of the described chamber or system. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

While illustrative embodiments have been illustrated and described, it will be appreciated that various changes can be made therein without departing from the spirit and scope of the invention.

The embodiments of the invention in which an exclusive property or privilege is claimed are defined as follows:

1. A nanoparticle comprising a solid metal core free, of ligands and non-metallic bonds, and further comprising an organic shell coupled to an outer surface of the solid metal core, wherein the organic shell further comprises a targeting moiety coupled to the nanoparticle, wherein the targeting moiety is configured to selectively bind to a target substrate.

2. The nanoparticle of claim 1, wherein the solid metal core comprises a metal chosen from an alkali metal, an alkaline earth metal, a transition metal, a post-transition metal, a lanthanide metal, an actinide metal, and a metalloid.

3. The nanoparticle of claim 1, wherein the solid metal core comprises a plurality of metal atoms of a single element.

4. The nanoparticle of claim 1, wherein the solid metal core is a mixed-metal core comprising two or more metal elements.

5. The nanoparticle of claim 4, wherein one or more of the two or more metal elements is radioactive.

6. The nanoparticle of claim 5, wherein the radioactive element is chosen from a radio-isotope of gold, indium, gadolinium, and platinum.

7. The nanoparticle of claim 1, wherein the solid metal core is magnetic.

8. The nanoparticle of claim 7, wherein the solid metal core comprises one or more magnetic elements chosen from cobalt, iron, nickel, manganese, and europium.

9. The nanoparticle of claim 1, wherein the organic shell is coupled directly to the solid metal core.

10. The nanoparticle of claim 9, wherein there is no ligand between the organic shell and the solid metal core.

11. The nanoparticle of claim 9, wherein the outer surface of the solid metal core has a zero valence state.

12. The nanoparticle of claim 9, wherein the outer surface of the solid metal core does not include metal oxides.

13. The nanoparticle of claim 1, further comprising a secondary shell coupled to an outer surface of the organic shell.

14. The nanoparticle of claim 13, wherein the secondary shell further comprises a plurality of metal nanoparticles coupled to the outer surface of the organic shell.

15. The nanoparticle of claim 1, wherein the targeting moiety includes components chosen from one or more of a restriction enzyme, an RNA/DNA modifying protein, an endonuclease, an RNA/DNA guided endonuclease, an exonuclease, a polymerase, a TALENS, an aptamer, an antibody, and a functional antibody fragment or derivative, Cas-9 and dCas-9.

16. The nanoparticle of claim 1, wherein the targeting moiety is coupled to the nanoparticle through a linker.

17. A device for low-pressure, solution-phase synthesis of metal nanoparticles, the device comprising:
   a single Schlenk line assembly;
   an all-glass chemical reaction environment coupled to the single Schlenk line assembly, the all-glass chemical reaction environment comprising:
   a vacuum-stopped back pressure overload valve;
   a plurality of back pressure-loaded injectors; and
   a reaction vessel; and
   a tri-valved vacuum interface coupled to the single Schlenk line assembly and configured to provide an extended headspace maintained under low-pressure to establish a vapor-phase gradient in the reaction vessel.

18. A method of tagging a target nucleic acid substrate with a nanoparticle, the method comprising assembling a targeted nanoparticle construct on the target nucleic acid substrate, wherein the targeted nanoparticle construct comprises a nanoparticle of claim 1 and a targeting moiety coupled thereto, wherein the targeting moiety selectively binds to a sequence in the target nucleic acid substrate.

19. A nanoparticle comprising a solid metal core free of ligands and non-metallic bonds, and further comprising an organic shell coupled to an outer surface of the solid metal core, wherein the organic shell further comprises a targeting moiety coupled to the nanoparticle, wherein the targeting moiety is configured to selectively bind to a target substrate, wherein the organic shell is coupled directly to the solid metal core, and wherein there is no ligand between the organic shell and the solid metal core.

20. A nanoparticle comprising a solid metal core free of ligands and non-metallic bonds, and further comprising an organic shell coupled to an outer surface of the solid metal core, wherein the organic shell further comprises a targeting moiety coupled to the nanoparticle, wherein the targeting moiety is configured to selectively bind to a target substrate, wherein the organic shell is coupled directly to the solid metal core, and wherein the outer surface of the solid metal core has a zero valence state.

* * * * *